US007862992B2

(12) United States Patent (10) Patent No.: US 7,862,992 B2
Murthy et al. (45) Date of Patent: Jan. 4, 2011

(54) DYNAMIC FERMENTATION CONTROLLER

(75) Inventors: Ganti Suryanarayana Murthy, Corvallis, OR (US); Vijay Singh, Savoy, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 652 days.

(21) Appl. No.: 11/851,205

(22) Filed: Sep. 6, 2007

(65) Prior Publication Data

US 2008/0064022 A1 Mar. 13, 2008

Related U.S. Application Data

(60) Provisional application No. 60/843,852, filed on Sep. 12, 2006.

(51) Int. Cl.
*C12Q 3/00* (2006.01)
*C12P 7/06* (2006.01)
*G06G 7/48* (2006.01)

(52) U.S. Cl. .................. 435/3; 435/161; 435/286.1; 707/11; 707/19; 707/21; 707/22

(58) Field of Classification Search .................. None
See application file for complete search history.

(56) References Cited

PUBLICATIONS

Bayrock, Dennis P., et al., "Inhibition of Yeast by Lactic Acid Bacteria in Continuous Culture: Nutrient Depletion and/or Acid Toxicity?", *Journal of Industrial Microbiology and Biotechnology*, vol. 31, No. 8, (Sep. 2004),pp. 362-368.
Bothast, Rodney J., "New Technologies in Biofuel Production", *Agricultural Outlook Forum*, (Feb. 24, 2005),24 Pages.
Horiuchi, Jun-Ichi "Fuzzy Modeling and Control of Biological Processes", *Journal of Bioscience and Bioengineering*, vol. 94, No. 6, (2002),pp. 574-578.
Kauffman, Kenneth J., et al., "Advances in Flux Balance Analysis", *Current Opinion in Biotechnology 2003*, vol. 14, (2003),pp. 491-496.
Nagodawithana, Tilak W., et al., "Effect of Dissolved Oxygen, Temperature, Initial Cell Count, and Sugar Concentration on the Viability of *Saccharomyces cerevisiae* in Rapid Fermentations", *Applied Microbiology*, vol. 28, No. 3, (1974),pp. 383-391.
Narendranath, N.V. et al., "Effects of Lactobacilli on Yeast-Catalyzed Ethanol Fermentations", *Applied and Environmental Microbiology*, vol. 63, No. 11, (Nov. 1997),pp. 4158-4163.
Pampulha, M. E., et al., "Combined Effect of Acetic Acid, pH and Ethanol on Intracellular pH of Fermenting Yeast", *Applied Microbiology and Biotechnology*, vol. 31, (1989),pp. 547-550.
Rausch, Kent D., et al., "The Future of Coproducts From Corn Processing", *Applied Biochemistry and Biotechnology*, vol. 128, (Feb. 2006),pp. 47-86.
"From Niche to Nation: Ethanol Industry Outlook 2006", *Renewable Fuels Association*, (Feb. 2006),24 Pages.
Shapouri, Hosein et al., "USDA's 2002 Ethanol Cost-of-Production Survey", *USDA Agricultural Economic Report* No. 841 (Jul. 2005),pp. 1-19.

Eckhoff, et al., "A Laboratory Wet-Milling Procedure to Increase Reproducibility and Accuracy of Product Yields", *Cereal Chemistry*, vol. 70, No. 6, (1998),pp. 723-727.
Cascante, et al., "Comparative Characterization of the Fermentation Pathway of *Saccharomyces cerevisiae* Using Biochemical Systems Theory and Metabolic Control Analysis: Model Definition and Nomenclature", *Mathematical Biosciences*, vol. 130, (1995),pp. 25-50.
Giuseppin, et al., "Metabolic Modeling of *Saccharomyces cerevisiae* Using the Optimal Control of Homeostasis: A Cybernetic Model Definition", *Metabolic Engineering*, vol. 2, available at <<http://www.idealibrary.com>>, Article ID 1999.0134,(2000),pp. 14-33.
Kapadi, et al., "Optimal Control of Fed-Batch Fermentation Involving Multiple Feeds Using Differential Evolution", *Process of Biochemistry*, vol. 9, (2004),pp. 1709-1721.
Lei, et al., "A Biochemically Structured Model for Saccharomyces Cerevisiae", *Journal of Biotechnology*, vol. 88, (2001),pp. 205-221.
Manners, David J., "Recent Developments in Our Understanding of Amylopectin Structure", *Carbohydrate Polymers*, vol. 11, (1989),pp. 87-112.
Singh, et al., "Comparison of Modified Dry-Grind Corn Processes for Fermentation Characteristics and DDGS Composition", *Cereal Chemistry*, vol. 82, No. 2, (2005),pp. 187-190.
Singh, et al., "Recovery of Fiber in the Corn Dry-Grind Ethanol Process: A Feedstock for Valuable Coproducts", *Cereal Chemistry*, vol. 76, No. 6, (1999),pp. 868-872.
Verduyn, et al., "Physiology of *Saccharomyces cerevisiae* in Anaerobic Glucose-Limited Chemostat Cultures", *Journal of General Microbiology*, vol. 136, (1990),pp. 395-403.
Verduyn, et al., "Energetics of *Saccharomyces cerevisiae* in Anaerobic Glucose-Limited Chemostat Cultures", *Journal of General Microbiology*, vol. 136, (1990),pp. 405-412.
Wahjudi, et al., "Quick Fiber Process: Effect of Mash Temperature, Dry Solids, and Residual Germ on Fiber Yield and Purity", *Cereal Chemistry*, vol. 77, No. 5, (2000),pp. 640-644.
Wang, et al., "Comparison of Enzymatic (E-Mill) and Conventional Dry-Grind Corn Processes Using a Granular Starch Hydrolyzing Enzyme", *Cereal Chemistry*, vol. 82, No. 6, (2005),pp. 734-738.
Whims, John "Corn Based Ethanol Costs and Margins: Attachment 1", *Agricultural Marketing Resource Center. Kansas State University, Manhattan, KS*, (2002),23 pages.
Ellis, R. P., et al., "Starch Production and Industrial Use", *Journal of the Science of Food and Agriculture*, vol. 77, No. 3, (1998),pp. 289-311.
Marchal, L. M., et al., "Monte-Carlo Simulation of α-Amylolysis of Amylopectin of Potato Starch", *Bioprocess and Biosystems Engineering*, vol. 24, No. 3, (2001),pp. 163-170.
Hizukuri, S. "Polymodal Distribution of the Chain Lengths of Amylopectins, and its Significance", *Carbohydrate Research*, vol. 147, No. 2, (1986),pp. 342-347.

(Continued)

*Primary Examiner*—Herbert J. Lilling

(57) ABSTRACT

One or more set point values are generated by a dynamic fermentation controller for one or more of temperature, pH, and enzyme dosage for a fermentation system. The one or more set point values are output to one or more controllers of the fermentation system. The generation of the one or more set point values and the outputting of the one or more set point values is repeated until a change in conditions in the fermentation system is detected.

8 Claims, 6 Drawing Sheets

OTHER PUBLICATIONS

Ivanova, V. N., et al., "Purification and Characterization of a Thermostable Alpha-Amylase from *Bacillus lincheniformis*", *Journal of Biotechnology*, vol. 28, No. 2-3, (1993),pp. 277-289.

Gadkar, K. G., et al., "Cybernetic Model Predictive Control of a Continuous Bioreactor with Cell Recycle", *Biotechnology Progress*, vol. 19, (2003),pp. 1487-1497.

Jones, K. D., et al., "Cybernetic Model of the Growth Dynamics of *Saccharomyces cerevisiae* in Batch and Continuous Cultures", *Journal of Biotechnology*, vol. 71, pp. 105-131, (1999),pp. 105-131.

Ramakrishna, R. et al., "Cybernetic Modeling Growth in Mixed, Substitutable Substrate Environments: Preferential and Simultaneous Utilization", *Biotechnology and Bioengineering*, vol. 42, (1996),pp. 141-151.

Straight, J. V., et al., "Cybernetic Modeling and Regulation of Metabolic Pathways. Growth on Complementary Nutrients", *Biotechnology Progress*, vol. 10, (1994),pp. 574-587.

Abbott, D. A., et al., "Buffering Capacity of Whole Corn Mash Alters Concentrations of Organic Acids Required to Inhibit Growth of *Saccharomyces cerevisiae* and Ethanol Production", *Biotechnology Letters*, vol. 26, (2004),pp. 1313-1316.

Beschkov, V. et al., "A Kinetic Model for Hydrolysis and Synthesis of Maltose, Isomaltose, and Maltotriose by Glucoamylase", *Biotechnology and Bioengineering*, vol. 26, (1984),pp. 22-26.

Chen, L. et al., "A Case Study of Adaptive Non Linear Regulation of Fed-Batch Biological Reactors", *Automatica*, vol. 31, (1995),pp. 55-56.

Cimander, C. et al., "Integration of Distributed Multi-Analyzer Monitoring and Control in Bioprocessing Based on a Real-Time Expert System", *Journal of Biotechnology*, vol. 103, (2003),pp. 237-248.

Ferreira, L. S., et al., "Aspects Concerning the Use of Biosensors for Process Control: Experimental and Simulation Investigations", *Computers & Chemical Engineering*, vol. 27, (2003),pp. 1165-1173.

Jeyamkondan, S. et al., "Microbial Growth Modeling with Artificial Neural Networks", *International Journal of Food Microbiology*, vol. 64, (2001),pp. 343-354.

Jaramulak, J. et al., "Neural Networks in Process Control: Model-Based and Reinforcement Trained Controllers", *Computers and Electronics in Agriculture*, vol. 18, (1997),pp. 149-166.

Jiahua, Z. "Kinetic Model for the Co-Action of β-Amylase and Debranching Enzymes in Production of Maltose", *Biotechnology and Bioengineering*, vol. 62, (1999),pp. 618-622.

Loureiro, V. et al., "Effects of Ethanol on the Maximum Temperature for Growth of *Saccharomyces cerevisiae*: A Model", *Biotechnology and Bioengineering*, vol. 24, (1982),pp. 1881-1884.

Meagher, M. M., et al., "Kinetics of Hydrolysis of Di- and Trisaccharides with Aspergillus Niger Glucoamylases i and ii", *Biotechnology and Bioengineering*, vol. 34, (1989),pp. 689-693.

Mishima, K. et al., "On-Line Monitoring of Cell Concentrations During Yeast Cultivations by Dielectric Measurements", *Journal of Fermentation and Bioengineering*, vol. 72, (1991),pp. 296-299.

Muthuswamy, K. et al., "Phase-Based Supervisory Control for Fermentation Process Development", *Journal of Process Control*, vol. 13, (2003),pp. 367-382.

Narendranath, N. V., et al., "Effects of Acetic Acid and Lactic Acid on the Growth of *Saccharomyces cerevisiae* in a Minimal Medium", *Journal of Industrial Microbiology and Biotechnology*, vol. 26, (2001),pp. 171-177.

Park, J. T., et al., "Effects of Substrate Branching Characteristics on Kinetics of Enzymatic Depolymerization of Mixed Linear and Branched Polysaccharides: 1. Amylose/Amylopectin α-Amylolysis", *Biotechnology and Bioengineering*, vol. 44, (1994),pp. 792-800.

Patnaik, P. R., "An Integrated Hybrid Neural System for Noise Filtering, Simulation and Control of a Fed-Batch Recombinant Fermentation", *Biochemical Engineering Journal*, vol. 15, (2003),pp. 165-175.

Paulocci-Jeanjean, D. et al., "Kinetics of Cassava Starch Hydrolysis Using Termamyl Enzyme", *Biotechnology and Bioengineering*, vol. 68, (1999),pp. 72-77.

Sainz, J. et al., "Modeling of Yeast Metabolism and Process Dynamics in Batch Fermentation", *Biotechnology and Bioengineering*, vol. 81, (2003),pp. 818-828.

Szederkenyi, G. et al., "Nonlinear Analysis and Control of a Continuous Fermentation Process", *Computers and Chemical Engineering*, vol. 26, (2002),pp. 659-670.

Tan, T. et al., "Ergosterol Production by Fed-Batch Fermentation of *Saccharomyces cerevisiae*", *Enzyme and Microbial Technology*, vol. 33, (2003),pp. 366-370.

Tester, R. F., et al., "Starch-Composition, Fine Structure and Architecture", *Journal of Cereal Science*, vol. 39, (2004),pp. 151-165.

Thatipamala, R. et al., "On-line Estimation and Adaptive Using State Equations for Continuous Production of Bioethanol", *Journal of Biotechnology*, vol. 48, (1996),pp. 179-190.

Thatipamala, R. et al., "Effects of High Product and Substrate Inhibitions on the Kinetics and Biomass and Product Yields During Ethanol Batch Fermentation", *Biotechnology and Bioengineering*, vol. 40, (1992),pp. 289-297.

Varner, J. et al., "Metabolic Engineering From a Cybernetic Perspective. 1. Theoretical Preliminaries", *Biotechnology Progress*, vol. 15, (1999),pp. 407-725.

Wiechert, W. et al., "13C Metabolic Flux Analysis", *Metabolic Engineering*, vol. 3, (2001),pp. 195-206.

Wojciechowski, P. M., et al., "Iteration Model of Starch Hydrolysis by Amylolytic Enzymes", *Biotechnology and Bioengineering*, vol. 75, (Dec. 5, 2001),pp. 530-539.

Wu, W. et al., "On-Line Optimal Control for Ethanol Production", *Journal of Biotechnology*, vol. 29, (Jun. 1993),pp. 257-266.

DYNAMIC FERMENTATION CONTROLLER

RELATED APPLICATIONS

This application claims the benefit of U.S. Provisional Application No. 60/843,852, filed Sep. 12, 2006, which is hereby incorporated by reference herein.

BACKGROUND

Producing ethanol from renewable resources has become an attractive solution to address current and future energy needs. One current technique for producing ethanol is a dry grind process that produces ethanol from renewable resources, such as corn. The dry grind process primarily uses a simultaneous saccharification and fermentation process in which an enzyme, glucoamylase, breaks down maltodextrins into fermentable sugars such as glucose and maltose. Yeast consumes these sugars, producing ethanol under anaerobic conditions. In current simultaneous saccharification and fermentation processes, process parameters are determined from prior experience and are fixed at static points.

SUMMARY

This Summary is provided to introduce subject matter that is further described below in the Detailed Description and the drawings. Accordingly, the Summary should not be considered to describe essential features nor used to limit the scope of the claimed subject matter.

A dynamic fermentation controller is discussed herein.

In accordance with one or more aspects of the dynamic fermentation controller, one or more set point values are generated for one or more of temperature, pH, and enzyme dosage for a fermentation system. The one or more set point values are output to one or more controllers of the fermentation system. The generation of the one or more set point values and the outputting of the one or more set point values is repeated until a change in conditions in the fermentation system is detected.

BRIEF DESCRIPTION OF THE DRAWINGS

The same numbers are used throughout the drawings to reference like features.

DETAILED DESCRIPTION

A dynamic fermentation controller is discussed herein. The controller dynamically sets process parameters, including values for temperature, pH, and enzyme dosage. A simultaneous saccharification and fermentation model is used to generate system state information that is input to the fermentation controller. The fermentation controller uses this system state information to dynamically generate set point values for temperature, pH, and enzyme dosage during the fermentation process. The controller updates these set point values as appropriate during the fermentation process based on changing conditions during the fermentation process.

Figure 1:
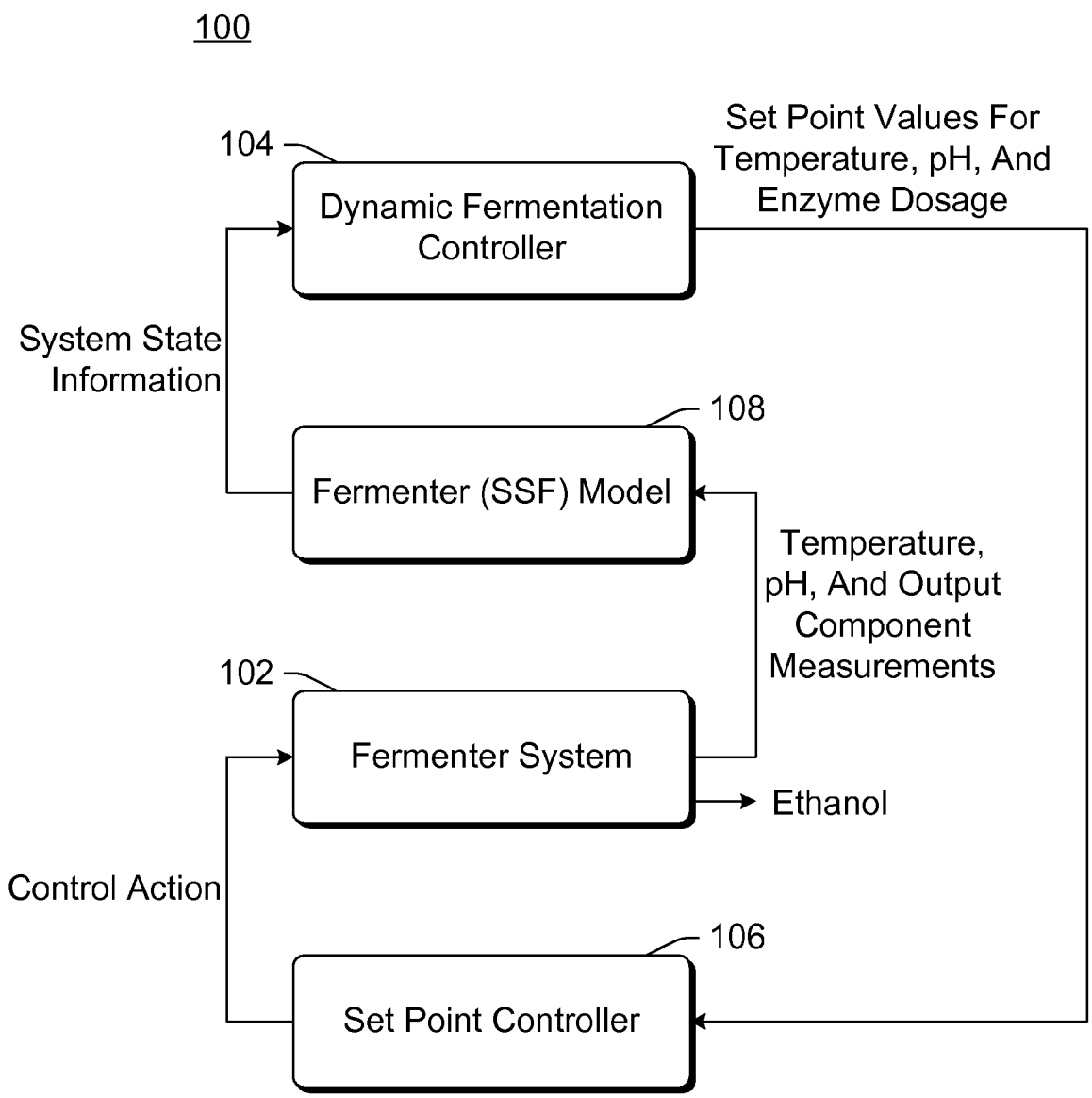
FIG. 1 is a block diagram illustrating an example fermentation system using a dynamic fermentation controller in accordance with one or more embodiments.

FIG. 1 is a block diagram illustrating an example fermentation system 100 using a dynamic fermentation controller. In system 100, a fermenter system 102 uses a simultaneous saccharification and fermentation (SSF) process to produce ethanol. This process typically produces ethanol from corn, although alternatively the process may operate based on other raw materials, such as wheat, rice, rye, barley, or potatoes. Dynamic fermentation controller 104 generates set point values for various process parameters for fermenter system 102, including set point values for temperature, pH, and enzyme dosage. Controller 104 generates these process parameters dynamically, changing the parameters as appropriate during the saccharification and fermentation process being performed by fermenter system 102.

The set point values from controller 104 are input to a set point controller 106 which controls various actions, such as the settings of pumps and/or valves, based on these set point values. These actions allow the temperature, pH, and enzyme dosage being used in the saccharification and fermentation process by fermenter system 102 to vary during the saccharification and fermentation process.

Fermenter system 102 produces a fermented mash, one component of which is ethanol. The temperature, pH, and amounts of the various components of the fermented mash are measured and input to a fermenter model 108. Fermenter model 108 models the simultaneous saccharification and fermentation process of fermenter system 102. Based on this modeling, fermenter model 108 generates system state information that is input to and used by dynamic fermentation controller 104 to determine the appropriate set point values for temperature, pH, and enzyme dosage.

Thus, as can be seen in FIG. 1, dynamic fermentation controller 104 alters the temperature, pH, and enzyme dosage as appropriate for fermenter system 102 during the simultaneous saccharification and fermentation process being performed by fermenter system 102. Controller 104 thus allows fermenter system 100 to adapt to changing conditions during the simultaneous saccharification and fermentation process of fermenter system 102, allowing for more efficient production of ethanol. This alteration of the temperature, pH, and enzyme dosage can be performed continuously while fermenter system 102 is producing ethanol, or alternatively can be performed at regular or irregular intervals while fermenter system 102 is producing ethanol. For example, the alteration of the temperature, pH, and enzyme dosage can be performed continually, every ten seconds, every minute, every minute when system 102 begins and then every five seconds after system 102 has been producing ethanol for at least a threshold amount of time or after at least a threshold amount of ethanol has been produced, and so forth.

The dynamic fermentation controller 104 is discussed herein primarily with reference to dynamically determining the appropriate set point values for temperature, pH, and enzyme dosage. Alternatively, controller 104 can set the appropriate set point values for only one or only two of the temperature, pH, and enzyme dosage.

The use of dynamic fermentation controller 104 over traditional fermentation processes can result in several advantages. Among these advantages are a reduction in the amount of enzyme used in the fermentation process, which equates to a financial savings in operating costs.

Figure 2:
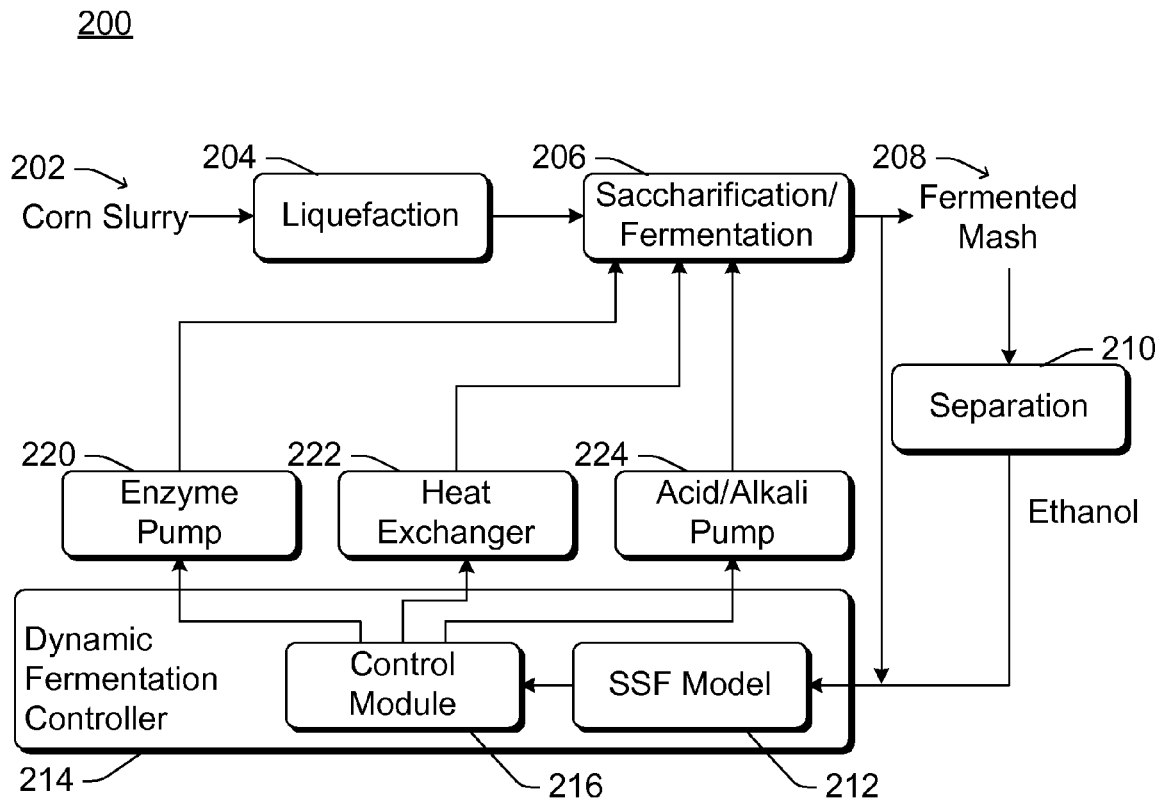
FIG. 2 is a block diagram illustrating an example fermentation system using a dynamic fermentation controller in accordance with one or more embodiments.

FIG. 2 is a block diagram illustrating an example fermentation system 200 using a dynamic fermentation controller. In system 200, a corn slurry 202 is generated by adding water to ground corn (typically having been previously ground in a hammer mill or other kinds of mill similar to a hammer mill). Corn slurry 202 is input to a liquefaction process 204, which adds an enzyme that breaks down long chain polymers in starch into shorter chain polymers (maltodextrins). Liquefaction process 204 also reduces the viscosity of the corn slurry. Any of a variety of different enzymes that break down long chain polymers in starch into shorter chain polymers can be used in liquefaction process 204, such as α-amylase.

The processed corn slurry is then input to a saccharification/fermentation process 206, where simultaneous saccharification and fermentation is performed. In saccharification/fermentation process 206 an enzyme breaks down the maltodextrins into fermentable sugars such as glucose and maltose. Any of a variety of enzymes can be used to break down the maltodextrins, such as glucoamylase. These generated fermentable sugars are then fermented by yeast to produce ethanol under anaerobic conditions.

Saccharification/fermentation process 206 generates a fermented mash 208, from which sugars, organic acids and alcohols are separated and quantified by analytical process 210. This separation and analysis can be performed in various manners, such as by using well-known high pressure liquid chromatography (HPLC) techniques. Various other components can also be separated from fermented mash 208, such as glucose, lactic acid, glycerol, and acetic acid.

The temperature and pH of the fermented mash 208 are also sensed and input to a simultaneous saccharification and fermentation model 212 of dynamic fermentation controller 214. The temperature and pH of the fermented mash 208 can be sensed after it is output by saccharification/fermentation process 206, or alternatively can be sensed while it is being processed by saccharification/fermentation process 206.

Additionally, measurements obtained from the output of separation process 210 are also input to simultaneous saccharification and fermentation model 212. These measurements obtained from the output of separation process 210 can be, for example, levels of ethanol, glucose, lactic acid, glycerol, and acetic acid. Simultaneous saccharification and fermentation model 212 models the simultaneous saccharification and fermentation being performed by saccharification/fermentation process 206, and generates system state information that is input to a control module 216 of controller 214. It should be noted that, although control module 216 and model 212 are illustrated as part of the same controller 214, module 216 and model 212 may alternatively be implemented as separate components and/or as parts of separate controllers.

Control module 216 uses the system state information it receives from simultaneous saccharification and fermentation model 212 to determine the appropriate set point values for temperature, pH, and enzyme dosage (e.g., glucoamylase dosage) for saccharification/fermentation process 206. The appropriate ones of these set point values are provided to enzyme pump 220, heat exchanger 222, and acid/alkali pump 224.

Enzyme pump 220 receives a set point value for enzyme dosage from control module 216. The enzyme dosage set point value indicates the amount of enzyme to be input to saccharification/fermentation process 206 by enzyme pump 220. The enzyme is added to process 206 during the saccharification/fermentation process, so enzyme pump 220 varies the amount of enzyme that is added to process 206 as the saccharification/fermentation process is being performed.

Heat exchanger 222 receives a set point value for temperature from control module 216. The temperature set point value indicates whether heat exchanger 222 should increase, decrease, or keep the current temperature for the saccharification/fermentation process 206. Heat exchanger 222 adds hot and/or cold water as appropriate to saccharification/fermentation process 206 as indicated by the temperature set point value. The amount of water and/or temperature of the water can also be varied based on the temperature set point value. The temperature of process 206 can change during the saccharification/fermentation process, so heat exchanger 222 varies the amount and/or temperature of water added to process 206 as the saccharification/fermentation process is being performed.

Acid/alkali pump 224 receives a set point value for pH from control module 216. The pH set point value indicates whether acid/alkali pump 224 should add an amount of acid or alkali to saccharification/fermentation process 206, as well as the amount of acid or alkali to add. Acid/alkali pump 224 adds the appropriate one of acid or alkali to process 206 as indicated by the pH set point value. The pH of process 206 can change during the saccharification/fermentation process, so acid/alkali pump 224 varies which of acid or alkali, as well as the amount of acid or alkali, to add to process 206 as the saccharification/fermentation process is being performed.

Figure 3:
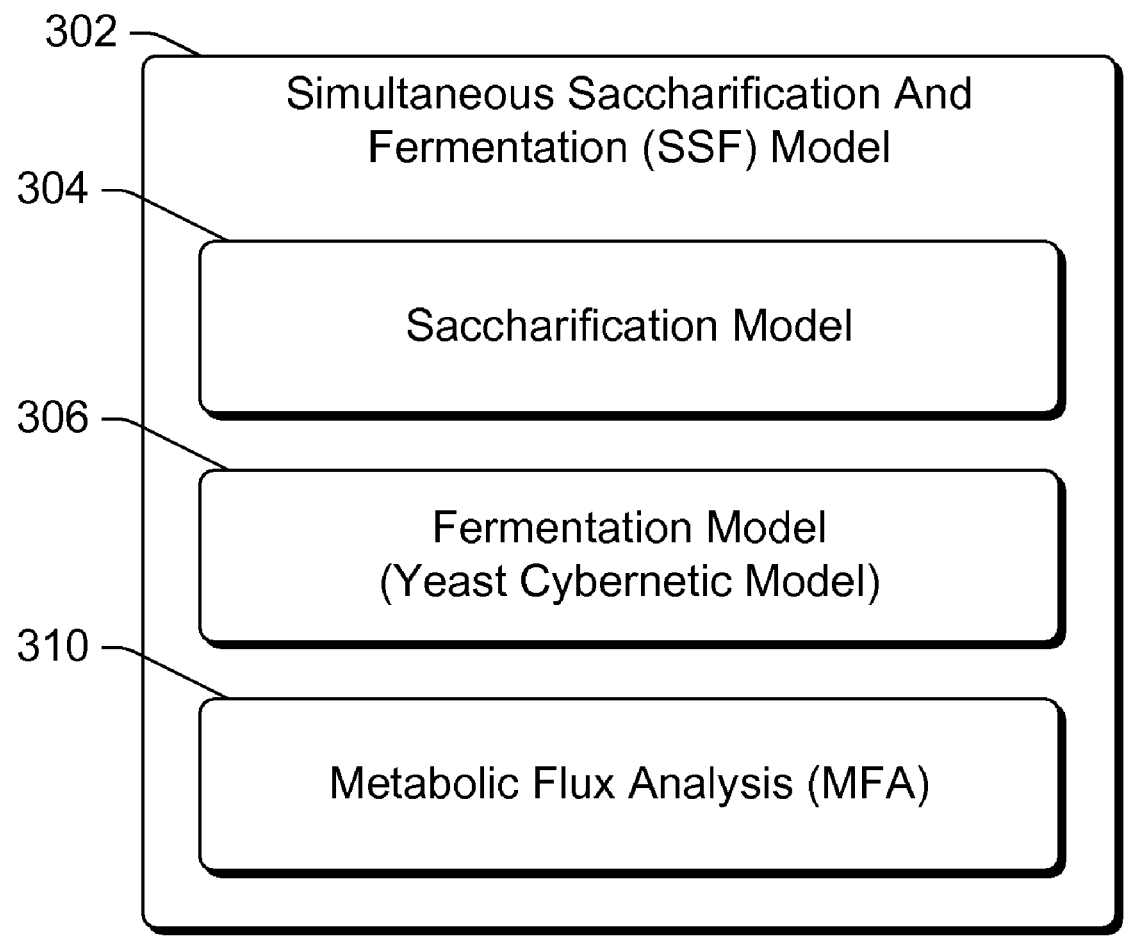
FIG. 3 illustrates an example simultaneous saccharification and fermentation model in accordance with one or more embodiments.

As discussed above, a simultaneous saccharification and fermentation (SSF) model (e.g., model 108 of FIG. 1 or model 212 of FIG. 2) models the simultaneous saccharification and fermentation performed by the fermenter system. FIG. 3 illustrates an example simultaneous saccharification and fermentation model in accordance with one or more embodiments.

It is to be appreciated that FIG. 2 illustrates an example fermentation system 200, and that various modifications can be made to system 200. For example, the temperature of saccharification/fermentation process 206 could be increased or decreased in any of a variety of different manners other than by using a heat exchanger 222. By way of another example, there could be separate pumps for acid and alkali rather than a single pump 224 as illustrated in FIG. 2, or the pH of saccharification/fermentation process 206 could be adjusted in any of a variety of different manners other than by use of pump 224.

In FIG. 3, SSF model 302 includes a saccharification model 304 and a fermentation model 306. Saccharification model 304 predicts the sugar concentration profiles at various saccharification times for glucose, maltose, maltotriose and $DP4^+$ in the mash. Fermentation model 306 simulates yeast metabolism during the SSF process. SSF model 302 also incorporates metabolic flux analysis 310 to estimate yeast cell mass using HPLC as discussed in more detail below.

Various different measurements or parameters are inputs to SSF model 302, including the yeast dosage, the temperature of the fermenter, the pH of the fermenter, the mash composition after liquefaction, the enzyme dosage, and the enzyme activity. The various input parameters are used by different parts of SSF model 302 during the modeling process, as discussed in more detail below. SSF model 302 can generate various outputs, such as the consumption rate of glucose and production rates of ethanol, yeast cell mass, acetic acid, lactic acid, and glycerol.

Saccharification model 304 predicts the sugar concentration in the mash, and this mash can be the initial liquefacted slurry (e.g., from liquefaction process 204 of FIG. 2), the fermented mash (e.g., fermented mash 208 of FIG. 2), or a modeled mash. In one or more embodiments, the fermented mash is initially modeled using a liquefaction model, and this modeled mash is used as a basis for the dynamic fermentation controller to determine its initial control actions. As discussed in more detail below, these actions can be subsequently modified during the saccharification and fermentation process by using HPLC to analyze the components of the fermented mash.

The liquefaction model or simulation comprises the following steps:

corn starch characterization modeling amylase and amylopectin molecules characterization of α-amylase and glucoamylase activities modeling α-amylase action on amylase and amylopectin In the corn starch characterization step, the starch is characterized by defining the amylase to amylopectin ratio as follows:

$$R = \left(\frac{\text{Mass of amylose}}{\text{Mass of amylopectin}}\right)$$

The ratio of amylase to amylopectin can be used to determine the relative number of molecules to be simulated. The relative number of amylase molecules ($RN_A$) is:

$$RN_A = \left(\frac{R}{1+R}\right)$$

And the relative number of amylopectin molecules ($RN_{AP}$) is:

$$RN_{AP} = \left(\frac{1}{1+R}\right)$$

In the modeling amylase and amylopectin molecules step, amylase is modeled as a linear molecule of varying DP (degree of polymerization). An initial DP of 500 is used, and a number between 0 and 19,500 of glucose units is added randomly or pseudo-randomly to reflect the DP range of amylase (500 to 20,000).

Amylopectin molecules are modeled based on the cluster model as discussed in "Polymodal distribution of the chain lengths of amylopectins, and its significance", by S. Hizukuri, Carbohydr. Res. 147:342-347 (1986). Amylopectin molecules consist of two types of side chains (A and B chains) and a backbone chain (C chain). The C chain forms the backbone of the entire molecule and has the only reducing end of the molecule. There are three types of B chains: B1 chains are attached to the C chain; B2 chains connect two B chains; and B3 chains have A chains linked to them. The A chains are free outer chains linked to inner B3 chains. A cluster is defined as the side chains attached to a C chain. A cluster width of n implies that on average there are n intermediate branches between the C chain and the A chains.

The lengths of the A ad B chains are dependent on the starch biological source. An example of chain length distribution in corn starch amylopectin is shown in Table I.

TABLE I

| Chain Type | Glucose Molecule Chain Length |
|---|---|
| A | 13 ± 2 |
| B1 | 22 ± 4 |
| B2 | 69 ± 13 |
| B3 | 42 ± 10 |
| C | 101 ± 16 |

The chain lengths in Table I are assumed to be distributed according to a Gaussian distribution. Branch locations are distributed according to Chi Square distribution whose degrees of freedom are governed by chain length and cluster width. Additional rules that govern branch locations are: 1) there cannot be branches in consecutive locations, and 2) there cannot be a linear chain connected by α(1-6) glycosidic bonds.

In the characterization of α-amylase and glucoamylase activities step, characteristics such as activity and stability at different pH and temperatures are well known, such as those discussed in "Purification and characterization of a thermostable α-amylase from *Bacillus lincheniform* is", by V. N. Ivanova et al., J. Biotehnol. 28:277-289 (1993). Enzyme activities are defined according to standards adopted by enzyme manufacturers and/or suppliers. For example, the enzyme activity unit for α-amylase (α-amylase solution *Bacillus licheniformis*, type XII-A saline solution 500 to 1000 units/mg protein, 1,4-α-D-glucan-glucanohydrolase, 9000-85-5, Sigma-Aldrich, St. Louis, Mo.) is defined as the amount of enzyme solution that will liberate 1.0 mg of maltose from starch in 3 minutes at H 6.9 at 20° C. The enzyme activity is 21,390 units/mL. The number of α(1-4) glycosidic bonds hydrolyzed by enzyme per molecule of amylase and amylopectin can be determined as follows.

The number of maltose (MW=342) molecules liberated by one unit of enzyme solution in 3 minutes is:

$$N_{h,std} = \left(\frac{6.023 \times 10^{23} \text{ molecules/mole}}{342 \text{ g/mole} \times 1000 \text{ mg/g} \times A_{aa,std}}\right)$$

where $A_{aa,std}$ represents the activity of the α-amylase under standard conditions. The number of bonds hydrolyzed per second per unit of enzyme then is:

$$N_{h,std} = \left(\frac{9.7839 \times 10^{15}}{A_{aa,std}}\right)$$

The number of bonds hydrolyzed by $E_m$ activity units of enzyme at specific operating conditions can be determined as:

$$N_h = \left(\frac{E_m \times A_{aa}}{A_{aa,std}}\right) \times 9.7839 \times 10^{15}$$

where $E_m$ represents the amount of enzyme (mL) added to the corn mash, $A_{aa}$ represents the activity of the α-amylase under operating conditions, and $A_{aa,std}$ represents the activity of the α-amylase under standard conditions.

Enzyme activity at a particular process condition (pH and temperature) is determined by interpolating values from:

$$A_{aa,std} = f1(A_{aa,max}, \text{Temperature}, \text{pH})$$

$$A_{aa} = f2(A_{aa,max}, \text{Temperature}, \text{pH})$$

where $A_{aa,max}$ represents the maximum activity of α-amylase.

The number of amylase molecules in the mash ($N_a$) and the number of amylopectin molecules in the mash ($N_{ap}$) are:

$$N_a = \left( \frac{W_{mash} \times S \times \left(\frac{X_{starch}}{100}\right) \times R \times 6.023 \times 10^{23}}{(1+R) \times 162 \times A_{avg,dp}} \right)$$

$$N_{ap} = \left( \frac{W_{mash} \times S \times \left(\frac{X_{starch}}{100}\right) \times 1 \times 6.023 \times 10^{23}}{(1+R) \times 162 \times AP_{avg,dp}} \right)$$

where $W_{mash}$ represents the total weight of the mash (g), S represents the solids concentration (wet basis) in the mash, $X_{starch}$ represents the starch content (%) of the corn, $A_{avg,dp}$ represents the average degree of polymerization of amylase, and $AP_{avg,dp}$ represents the average degree of polymerization of amylopectin.

The number of bonds hydrolyzed per amylase molecule is:

$$N_{hA} = \left( \frac{N_h \times N_a}{N_a + N_{ap}} \right)$$

where $N_h$ represents the number of bonds hydrolyzed by $E_m$ (mL) of enzyme per second, $N_a$ represents the number of amylase molecules in the mash, and $N_{ap}$ represents the number of amylopectin molecules in the mash. Similarly, the number of bonds hydrolyzed per amylopectin molecule is:

$$N_{hAP} = \left( \frac{N_h \times N_a}{N_a + N_{ap}} \right)$$

The glucoamylase characteristics are obtained from data sheets published by the manufacturer. For example, one Novo amyloglucosidase (AMG) unit was defined as the amount of enzyme that releases one micro mole of maltose per minute under standard conditions. The activity of the glucoamylase at standard conditions is:

$$A_{ga,std} = A_{ga,max} \times T_{effect} \times pH_{effect}$$

where $A_{ga,max}$ represents the maximum activity of glucoamylase, $T_{effect}$ represents the effect of temperature on enzyme activity, and $pH_{effect}$ represents the effect of pH on enzyme activity. As an example, characteristics of glucoamylase from Sigma-Aldrich (St. Louis, Mo.) in the operating range of temperature (T)<67° C. and pH<4.8, as indicated in data sheets published by the manufacturer, are:

$$T_{effect} = -4.49 \times 10^{-4} T^3 + 0.065511 T^2 - 1.383586 T + 31.698362$$

$$pH_{effect} = -16.284015 pH^2 + 113.84832 pH - 99.3048032 \text{ if } pH < 3.7$$

$$pH_{effect} = 0.874418 pH^3 - 9.709083 pH^2 - 2.734213 pH + 203.087742 \text{ if } pH > 3.7$$

As another example, characteristics of glucoamylase from Genencor (Palo Alto, Calif.) in the operating range of T<62° C. and pH<6.5, as indicated in data sheets published by the manufacturer, are:

$$T_{effect} = -3 \times 10^{-4} T^3 + 0.0307 T^2 - 2.2349 T + 41.186$$

$$pH_{effect} = 0.78514 pH^4 - 14.074 pH^3 + 80.405 pH^2 - 167.01 pH + 179.18$$

In the modeling α-amylase action on amylase and amylopectin step, a Monte Carlo simulation method is used for enzymatic hydrolysis of amylase and amylopectin. The Monte Carlo simulation method is discussed, for example, in "Monte-carlo simulation of α-amylolysis of amylopectin of potato starch", by L. M. Marchal et al., Bioproc. Eng. 24:163-170 (2001). Hydrolysis is performed on each molecule, and a sequence of random or pseudo-random numbers (less than or equal to the DP of the molecule) with uniform probability distribution is generated. Bonds at the locations indicated by the generated random or pseudo-random numbers are hydrolyzed depending on the rules for enzymatic action: 1) glucose units that have associated branch chains cannot be hydrolyzed, 2) branch location to be hydrolyzed should be at least two units away from the end of the chain, and 3) a bond cannot be broken twice. At the end of simulation of all (or alternatively at least some) of the molecules, the dextrose equivalent (DE) and the average molecular weight (AMW) are calculated as follows:

$$DE = \left( \frac{100 \times 180 \times (\text{Number of bonds hydrolyzed} + 1)}{162 \times \text{Total } DP + 18 \times (\text{Number of bonds hydrolyzed} + 1)} \right)\%$$

$$AMW = \left( \frac{162 \times \text{Total } DP}{\text{Number of bonds hydrolyzed}} + 18 \right) \text{g/mol}$$

Returning to saccharification model 304, saccharification model 304 predicts the sugar concentration in the mash as follows. Maltodextrin profiles obtained from the liquefaction model, or alternatively obtained elsewhere, are input to saccharification model 304. A nonreducing end is selected randomly or pseudo-randomly from available nonreducing ends of maltodextrin molecules. Bonds are hydrolyzed depending on the rules for enzymatic action: 1) a glucose unit that has a branch chain associated with it has 20 times lower probability to be hydrolyzed, and 2) for molecules with DP less than or equal to 5, the probability of hydrolysis is decreased with the decrease in DP of the molecule.

The liquefaction model discussed above predicts the sugar concentration profiles at various saccharification times for glucose, maltose, maltotriose, and DP4$^+$ in the mash. The concentration of various sugars is calculated based on sugars produced during the hydrolysis (during the liquefaction) discussed above.

$$C_{Glucose} = 100 \left( \frac{G_{total} Starch_{dp}}{DP_{simulated} 6.023 \times 10^{23}} \right) \left( \frac{180}{W_{mash}(1-S)} \right)$$

$$C_{Maltose} = 100 \left( \frac{M_{total} Starch_{dp}}{DP_{simulated} 6.023 \times 10^{23}} \right) \left( \frac{342}{W_{mash}(1-S)} \right)$$

$$C_{Maltriose} = 100 \left( \frac{MT_{total} Starch_{dp}}{DP_{simulated} 6.023 \times 10^{23}} \right) \left( \frac{522}{W_{mash}(1-S)} \right)$$

$$C_{DP4^+} = 100 \left( \frac{DP4^+_{total} Starch_{dp}}{DP_{simulated} 6.023 \times 10^{23}} \right) \left( \frac{162}{W_{mash}(1-S)} \right)$$

where $C_{Glucose}$ represents the concentration of glucose (% db) in the mash, $G_{total}$ represents the total number of glucose molecules in the mash, $Starch_{dp}$ represents the total number of starch molecules in the mash, $DP_{simulated}$ represents the total number of glucose molecules in the mash, $C_{Maltose}$ represents the concentration of maltose (% db) in the mash, $M_{total}$ represents the total number of maltose molecules in the mash, $C_{Maltotriose}$ represents the concentration of maltotriose (% db) in the mash, $MT_{total}$ represents total number of maltotriose molecules in the mash, $C_{DP4^+}$ represents the concentration of $DP4^+$ in the mash, and $DP4_{total}^+$ represents the total number of $DP4^+$ molecules in the mash.

Fermentation model 306 is based on a yeast cybernetic model. The yeast cybernetic model is based on the yeast growth process, which can be divided into catabolism and anabolism. During catabolism, sugars are converted into energy (ATP), redox (NADH) precursors and building blocks for cellular components. During anabolism, these precursors are used to build cellular components such as proteins, DNA, RNA, lipids and other macromolecules. Apart from anabolism, energy and redox precursors are used for performing cellular functions such as maintenance of internal pH and nutrient transport against concentration gradient across cell membrane.

Yeast metabolism consisting of >1000 reactions is lumped into four reactions pathways ($r_1$, $r_2$, $r_3$, and $r_4$) catalyzed by enzymes having concentrations $e_1$, $e_2$, $e_3$, and $e_4$. These concentrations $e_1$, $e_2$, $e_3$, and $e_4$ can have any of a variety of values, and in one or more embodiments have a default value that is very small (e.g., $10^{-8}$). The yeast cybernetic model includes three pathways (with reaction rates $r_1$, $r_2$, and $r_4$) that produce necessary precursors in catabolic pathways as well as building new cells from precursor molecules in an anabolic pathway (with reaction rate $r_3$). Two reactions (with reaction rates $r_1$, and $r_4$) represent the anaerobic and aerobic respiration options for producing energy metabolite precursors while another reaction (with reaction rate $r_2$) is a lumped reaction for producing structural precursor metabolites. The growth reaction (with reaction rate $r_3$) is promoted to achieve the evolutionary goal of high growth. For ease of explanation $r_i$ refers to the reaction rate of the $i^{th}$ pathway and is also used to identify the $i^{th}$ pathway.

The reaction rate $r_1$ determines the rate of conversion of glucose into energy metabolite precursors (EM) using the anaerobic pathway. This reaction is assumed to follow Monod kinetics with respect to glucose and is further dependent on enzyme $e_1$, a key enzyme for the pathway. As used herein, $e_i$ refers to the concentration of the $i^{th}$ enzyme (g/g of cell mass) catalyzing reaction $r_i$. The reaction rate $r_1$ is:

$$r_1 = \mu_1 e_1 \left(\frac{G}{K_1 + G}\right)\left(1 - H_{G,150}\left(\frac{G-150}{330-150}\right)\right)\left(1 - H_{E,95}\left(\frac{E-95}{150-95}\right)\right)$$

where $\mu_1$ represents a growth rate constant for the pathway, G represents the concentration of glucose (g/L), $K_1$ represents a Monod model constant, and E represents the concentration of ethanol (g/L). The growth rate constant $\mu_1$ can have different values, and in one or more embodiments this constant has the value 0.20. The constant $K_1$ can have different values, and in one or more embodiments this constant has the value 100. $H_{a,b}$ represents the Heavyside function, which is:

$$H_{a,b} = \begin{cases} 1 \text{ if } a > b \\ 0 \text{ if } a \le b \end{cases}$$

The second rate equation $r_2$ lumps conversion of glucose into structural metabolite precursors (SM). Similar to $r_1$, this reaction is repressed by high substrate and product concentrations. The reaction is catalyzed by a key enzyme having concentration of $e_2$, whose activity and synthesis are regulated by cybernetic parameters $v_2$ and $\mu_2$, respectively. The reaction rate $r_2$ is:

$$r_2 = \mu_2 e_2 \left(\frac{G}{K_2 + G}\right)\left(1 - H_{G,150}\left(\frac{G-150}{330-150}\right)\right)\left(1 - H_{E,95}\left(\frac{E-95}{150-95}\right)\right)$$

where $\mu_2$ represents a growth rate constant for the pathway, and $K_2$ represents a Monod model constant. The growth rate constant $\mu_2$ can have different values, and in one or more embodiments this constant has the value 0.25. The constant $K_2$ can have different values, and in one or more embodiments this constant has the value 100.

Reaction kinetics for the production of cell mass from energy and structural precursor metabolites is given by $r_3$. The key enzyme concentration $e_3$ catalyzes the pathway reactions; activity and synthesis of $e_3$ are controlled by cybernetic variables $v_3$ and $\mu_3$, respectively. The reaction rate $r_3$ is:

$$r_3 = \mu_3 e_3 \left(\frac{EM}{K_3 + EM}\right)\left(\frac{SM}{K_4 + SM}\right)$$

where $\mu_3$ represents a growth rate constant for the pathway $r_3$, $K_3$ and $K_4$ represent Monod model constants, EM represents the concentration of energy metabolite precursors (g/L), and SM represents the concentration of structural metabolite precursors (g/L). The growth rate constant $\mu_3$ can have different values, and in one or more embodiments this constant has the value 0.40. The constants $K_3$ and $K_4$ can have different values, and in one or more embodiments $K_3$ and $K_4$ both have the value 10.

The fourth rate equation $r_4$ describes the aerobic fermentation where the glucose is converted into the EM without the production of ethanol. The reaction rate follows modified Monod kinetics with rate dependent on glucose and oxygen concentrations. Further, the reaction is catalyzed by the key enzyme $e_4$. The activity and synthesis of $e_4$ are controlled by cybernetic variables $v_4$ and $\mu_4$, respectively. The reaction rate $r_4$ is:

$$r_4 = \mu_4 e_4 \left(\frac{G}{K_1 + G}\right)\left(\frac{O}{K_5 + O}\right)$$

where $\mu_4$ represents a growth rate constant for the pathway $r_4$, $K_1$ and $K_5$ represent Monod model constants, and O represents the concentration of oxygen (g/L). The growth rate constant $\mu_4$ can have different values, and in one or more embodiments this constant has the value 0.30. The constant $K_5$ can have different values, and in one or more embodiments this constant has the value 0.001.

The cybernetic regulation of reaction pathways can be derived by observing that reaction rates $r_1$ and $r_2$ are complementary since both SM and EM are essential for growth. Reactions $r_1$ and $r_4$ are substitutable pathways, since the EM can be produced by aerobic/anaerobic fermentation pathways. A value v refers to the cybernetic variable controlling enzyme activity, and a value $\psi$ refers to the cybernetic variable controlling enzyme synthesis. Reaction rate $r_3$ is regulated such that $\psi_3=1$ and $v_3=1$ to achieve the overall objective of high growth. Reaction $r_1$ is part of two pathways, one of which is complementary and the other substitutable. Therefore, overall pathway regulation is determined by the product of the regulatory coefficients obtained from the aerobic and anaerobic processes.

For substitutable pathway $r_1$, a value $v_1'$ is calculated as follows:

$$v_1' = \left(\frac{r_1}{\text{Max}(r_1, r_4)}\right)$$

where Max(a,b) refers to the maximum value of a and b. For complementary pathway $r_1$, a value $v_1''$ is calculated as follows:

$$v_1'' = \left(\frac{r_1/EM}{\text{Max}(r_1/EM, r_2/SM)}\right)$$

The overall regulation for substitutable and complementary pathways $r_1$ is represented as $v_1$ as follows:

$$v_1 = v_1' v_1''$$

For complementary pathway $r_2$, a value $v_2$ is calculated as follows:

$$v_2 = \left(\frac{r_2/EM}{\text{Max}(r_1/EM, r_2/SM)}\right)$$

And, for substitutable pathway $r_4$, a value $v_4$ is calculated as follows:

$$v_4 = \left(\frac{r_4}{\text{Max}(r_1, r_4)}\right)$$

Additionally, for substitutable pathway $r_1$, a value $\psi_1'$ is calculated as follows:

$$\psi_1' = \left(\frac{r_1}{r_1 + r_4}\right)$$

For complementary pathway $r_1$, a value $\psi_1''$ is calculated as follows:

$$\psi_1'' = \left(\frac{r_1/EM}{r_1/EM, r_2/SM}\right)$$

The overall regulation for substitutable and complementary pathways $r_1$ is represented as $\psi_1$ as follows:

$$\psi_1 = \psi_1' \psi_1''$$

For complementary pathway $r_2$, a value $\psi_2$ is calculated as follows:

$$\psi_2 = \left(\frac{r_2/SM}{r_1/EM, r_2/SM}\right)$$

And, for substitutable pathway $r_4$, a value $\psi_4$ is calculated as follows:

$$\psi_4 = \left(\frac{r_4}{r_1 + r_4}\right)$$

Additionally, the yeast cybernetic model includes a system of equations for dynamic chemical species balance. The system of equations, and the fermentation systems discussed herein, can be batch, fed batch, or continuous reactor configurations. In a continuous fermenter, nutrients are fed at a particular dilution rate into the fermenter, and fermenting mash is removed from the fermenter at a particular rate. In a typical continuous fermenter, a well mixed solution is assumed. In a batch fermenter, a dilution rate is set to zero and there is no inflow or outflow of fermenting mash. In a fed batch fermenter, there is constant inflow of feed; however, there is no outflow of fermenting mash.

The rate of yeast cell mass growth is dependent on the yeast cell mass already present and the availability of the SM and EM. Yeast cell mass growth is an autocatalytic reaction with reaction rate $r_3$. The rate of change of yeast cell mass is represented as:

$$\frac{dX}{dt} = (r_3 - D)X + \eta_3(0.1212T) + \eta_4\left(-H_{T,33}\exp\left(\frac{T-33}{37-33}\right)\right)$$

where D represents the dilution rate (L/second), $\eta_i$ represents assumed proportionality constants for including environmental effects, E represents the concentration of ethanol (g/L), and T represents the mash/fermenter temperature. The proportionality constants $\eta_i$ can have different values, and in one or more embodiments $\eta_3$ has a value of 0.001, and $\eta_4$ has a value of 0.001.

Glucose can be utilized to produce energy and structural metabolite precursors via reactions $r_1$, $r_2$, or $r_4$. The utilization of glucose is represented as:

$$\frac{dG}{dt} = -\left(\frac{r_1 v_1}{Y_1} + \frac{r_2 v_2}{Y_2} + \frac{r_4 v_4}{Y_3}\right)X + (G_0 + G)D$$

where $Y_i$ represents the yield coefficient for the $i^{th}$ pathway, X represents the concentration of cell mass (g/L), $G_0$ represents the initial glucose concentration (g/L), and G represents the concentration of glucose (g/L).

The rate of change of ethanol $$\frac{dE}{dt}$$

and the rate of change of oxygen $$\frac{dO}{dt}$$

during conversion of glucose to EM are represented as:

$$\frac{dE}{dt} = \left(\phi_1 \frac{r_1 v_1}{Y_1}\right)X - ED$$

$$\frac{dO}{dt} = -\left(\phi_2 \frac{r_4 v_4}{Y_3}\right)X + (K_{La}O^* - DO)$$

where $\phi_1$ represents coefficients for production of ethanol in reaction $r_1$, $\phi_2$ represents coefficients for consumption of oxygen in reaction $r_4$, $K_{La}$ represents the mass transfer coefficient for oxygen transfer in the fermenter, $O^*$ represents dissolved oxygen concentration limit (g/L), and O represents the concentration of oxygen (g/L). The coefficients for production of ethanol in reaction $r_1$ and the coefficients for consumption of oxygen in reaction $r_4$ can have different values, and in one or more embodiments $\phi_1$ and $\phi_2$ both have values of 0.51.

The EM produced under aerobic and anaerobic reactions $r_1$ and $r_4$, respectively, are utilized to produce more cell mass through $r_3$. These precursors are utilized for cellular maintenance functions whose rate of consumption is dependent on environmental conditions. The changes in energy metabolite precursors (EM) are represented as:

$$\frac{dEM}{dt} = \left(r_1 v_1 + r_4 v_4 - \frac{r_3 v_1}{\alpha_1}\right)X - \eta_1\left(\frac{1229.56 C_{aa}}{10^{pH-4.71}+1}\right)$$

where $\alpha_1$ represents a coefficient for production of a unit cell mass from EM in reaction $r_3$, $C_{aa}$ represents the concentration of acetic acid (g/L), and pH represents the pH of the mash/fermenter. The proportionality constant $\eta_1$ can have different values, and in one or more embodiments $\eta_1$ has a value of 0.001. The coefficient $\alpha_1$ for production of a unit cell mass from EM in reaction $r_3$ can have different values, and in one or more embodiments $\alpha_1$ has a value of 1.0.

SM precursors are produced in an enzyme catalyzed reaction from glucose. Production is substrate inhibited and influenced by ethanol concentration. SM precursors are utilized to created more yeast cell mass. The changes in structural metabolite precursors (SM) are represented as:

$$\frac{\partial SM}{\partial t} = \left(r_2 v_2 - \frac{r_3 v_1}{\alpha_2}\right)X - \eta_2 H_{pH,5.0}(0.725 \text{ pH})$$

where $\alpha_2$ represents a coefficient for production of a unit cell mass from SM in reaction $r_3$. The proportionality constant $\eta_2$ can have different values, and in one or more embodiments $\eta_2$ has a value of 0.01. The coefficient $\alpha_2$ for production of a unit cell mass from SM in reaction $r_3$ can have different values, and in one or more embodiments $\alpha_2$ has a value of 1.0.

Additionally, the rate of change of enzyme $e_i$ for pathway $r_i$ is represented as follows:

$$\frac{de_1}{dt} = \psi_1\left(\frac{G}{K_1+G}\right) - e_1\beta + \alpha^*$$

$$\frac{de_2}{dt} = \psi_2\left(\frac{G}{K_1+G}\right) - e_2\beta + \alpha^*$$

$$\frac{de_3}{dt} = \psi_3\left(\frac{EM}{K_2+EM}\right)\left(\frac{SM}{K_3+SM}\right) - e_3\beta + \alpha^*$$

$$\frac{de_4}{dt} = \psi_4\left(\frac{G}{K_1+G}\right)\left(\frac{O}{K_4+O}\right) - e_4\beta + \alpha^*$$

where $K_i$ represents the Monod model constant for pathway $r_i$, $\beta$ represents the constant intracellular enzyme breakdown rate, and $\alpha^*$ represents the constant intracellular enzyme synthesis rate. The constant intracellular enzyme breakdown rate $\beta$ and the constant intracellular enzyme synthesis rate $\alpha^*$ can have different values, and in one or more embodiments $\beta$ has a value of 0.1, and $\alpha^*$ has a value of 0.01.

The simultaneous saccharification and fermentation model 302 incorporates both the saccharification model 304 and fermentation model 306. Saccharification is an enzymatic hydrolysis reaction catalyzed by exoenzyme glucoamylase, and fermentation is a yeast growth process. Glucoamylase, an exoenzyme, cleaves $\alpha(1-4)$ bonds from the nonreducing end and releases glucose molecules. Under conditions of substrate saturation, the reaction rate is dependent on enzyme activity and amount. Since substrate concentration is many times more than enzyme concentration during SSF (except towards the end of the process), it is assumed that substrate saturation conditions exist during SSF. This can be modeled as:

$$\frac{dGP}{dt} = -GA_{activity} GA$$

where $GA_{activity}$ represents the activity of glucoamylase at given pH and temperature, and GA represents the concentration of glucoamylase (g/L).

Accordingly, the model for SSF based on the yeast model and saccharification model discussed above is:

$$\frac{dX}{dt} = (r_3 - D)X + \eta_3(0.1212T) + \eta_4\left(-H_{T,33}\exp\left(\frac{T-33}{37-33}\right)\right)$$

$$\frac{dGP}{dt} = -GA_{activity} GA$$

$$\frac{dG}{dt} = -\left(\frac{r_1 v_1}{Y_1} + \frac{r_2 v_2}{Y_2} + \frac{r_4 v_4}{Y_3}\right)X + (G_0 - G)D + \eta_0 H_{GP,0}\left(\frac{-dGP}{dt}\right)$$

$$\frac{dE}{dt} = \left(\phi_1 \frac{r_1 v_1}{Y_1}\right)X - ED$$

$$\frac{dO}{dt} = -\left(\phi_2 \frac{r_4 v_4}{Y_3}\right)X + (K_{La}O^* - DO)$$

$$\frac{dEM}{dt} = \left(r_1 v_1 + r_4 v_4 - \frac{r_3 v_1}{\alpha_1}\right)X - \eta_1\left(\frac{1229.56 C_{aa}}{10^{pH-4.71}+1}\right)$$

$$\frac{dSM}{dt} = \left(r_2 v_2 - \frac{r_3 v_1}{\alpha_2}\right)X - \eta_2 H_{pH,5.0}(0.725 \text{ pH})$$

$$\frac{de_1}{dt} = \psi_1\left(\frac{G}{K_1+G}\right) - e_1\beta + \alpha^*$$

$$\frac{de_2}{dt} = \psi_2\left(\frac{G}{K_1+G}\right) - e_2\beta + \alpha^*$$

$$\frac{de_3}{dt} = \psi_3\left(\frac{EM}{K_2+EM}\right)\left(\frac{SM}{K_3+SM}\right) - e_3\beta + \alpha^*$$

$$\frac{de_4}{dt} = \psi_4\left(\frac{G}{K_1+G}\right)\left(\frac{O}{K_4+O}\right) - e_4\beta + \alpha^*$$

Various parameters are discussed in the modeling calculations discussed above. It is to be appreciated that these parameters can have a variety of different values. Table II illustrates examples of parameters that can be used for SSF model 302.

TABLE II

| Parameter | Example Value |
|---|---|
| $\alpha^*$ (g/L · s) | 0.01 |
| B (1/s) | 0.1 |
| D (1/s) | 0.0 |
| $K_{La}$ (1/s) | 350 (aerobic fermentation) |
| $K_{La}$ (1/s) | 0 (anaerobic fermentation) |
| $K_1, K_2$ (g/L) | 100 |
| $K_3, K_4$ (g/L) | 10 |
| $K_5$ (g/L) | 0.001 |
| $Y_1$ | 0.08 |
| $Y_2$ | 0.25 |
| $Y_3$ | 0.1 |
| $\eta_0$ | 0.004 |
| $\eta_1$ | 0.001 |
| $\eta_2$ | 0.01 |
| $\eta_3$ | 0.001 |
| $\eta_4$ | 0.01 |
| $\phi_1$ | 0.56 |
| $\phi_2$ | 0.51 |
| $\mu_1$ (1/s) | 0.25 |
| $\mu_2$ (1/s) | 0.40 |
| $\mu_3$ (1/s) | 0.30 |
| $\alpha_1$ | 1.0 |
| $\alpha_2$ | 1.0 |

Metabolic flux analysis (MFA) 310 uses HPLC data to obtain estimates of yeast cell mass (X). MFA is a technique to estimate the unmeasured fluxes based on measured fluxes and internal cellular reaction stoichiometery. Most cell reactions occur over times scales of 2 to 3 minutes, and thus can be considered to be pseudo steady state compared to yeast cell growth which typically occurs over times scales of about 1 to 2 hours. The MFA 310 model is based on the model for yeast metabolism discussed in "A biochemically structured model for *Saccharomyces cerevisiae*", by F. Lei et al., J. Biotechnol. 88:205-221 (2001).

In the MFA 310 model, the stoichiometry for the model including six catabolic reactions (Q4, Q3, Q5, Q8, Q7, and Q6) and one anabolic reaction (Q2) is as follows:

$Q2$: $CH_{1.82}O_{0.485}N_{0.16} + alpha\,CO_2 -$
$Y_{xATP} + Y_{xNADH}NADH + (1 + \alpha)CH_2 = 0$ $Q4$: $CH_{\frac{8}{3}}O - \frac{1}{3}ATP - \frac{1}{3}NADH - CH_2O = 0$ $Q3$: $CH_{\frac{4}{3}}O + \frac{1}{3}ATP + \frac{1}{3}NADH - CH_2O = 0$ $Q5$: $\frac{2}{3}CH_2O_{0.5} + \frac{1}{3}CO_2 - CH_{\frac{4}{3}}O = 0$ $Q8$: $CH_3O_{0.5} - \frac{1}{2}NADH - CH_2O_{0.5} = 0$ $Q7$: $CH_2O + \frac{1}{2}NADH - CH_2O_{0.5} = 0$ $Q6$: $CO_2 + \frac{5}{3}NADH + \frac{1}{3}ATP - CH_{\frac{4}{3}} = 0$ where $Y_{xATP}$ represents cell mass yield coefficient on ATP, $Y_{xNADH}$ represents cell mass yield coefficient on NADH, ATP represents reactions describing constraints for use of energy resources, and NADH represents reactions describing constraints for use of redox resources.

The mass balance around the branch points for glucose, pyruvate, acetaldehyde, and NADH yields with the reaction fluxes Q1 to Q8 expressed as the product of stoichiometric matrix (St) and flux vector matrix (Q) is:

$$St \times Q = \begin{bmatrix} 0 & 0 & 1 & 0 & -1 & -1 & 0 & 0 \\ 0 & 0 & 0 & 0 & 0.67 & 0 & -1 & -1 \\ 0 & 0.23 & 1/3 & -1/3 & 0 & 5/3 & 0.5 & -0.5 \\ 1 & -1.21 & -1 & -1 & 0 & 0 & 0 & 0 \end{bmatrix} \begin{pmatrix} Q1 \\ Q2 \\ Q3 \\ Q4 \\ Q5 \\ Q6 \\ Q7 \\ Q8 \end{pmatrix} \begin{matrix} \text{Pyruvate} \\ \text{Acetaldehyde} \\ NADH \\ \text{Glucose} \end{matrix}$$

The average fluxes Q1, Q4, Q7, and Q8 can be obtained from HPLC measurements as follows. Let $G_1$ and $G_2$ be the glucose concentrations measured at $t_1$ and $t_2$ times, respectively. Let $g_1$ and $g_2$ be the glucose concentrations estimated based on saccharification model (using Monte Carlo techniques described above) at times $t_1$ and $t_2$, respectively. Mean glucose flux (Q1) expressed in terms of carbon moles utilized for the time between $t_1$ and $t_2$ is:

$$Q1 = \left( \frac{(G_1 + g_1) - (G_2 + g_2)}{t_1 - t_2} \right) \left( \frac{1}{G_{MW}} \right)$$

where $G_{MW}$ represents the molecular weight of glucose (g/mol). Let $E_1$ and $E_2$ be the glucose concentrations measured at $t_1$ and $t_2$ times, respectively. Mean ethanol flux (Q8) expressed in terms of carbon moles utilized for the time between $t_1$ and $t_2$ is:

$$Q8 = \left( \frac{E_1 - E_2}{t_1 - t_2} \right) \left( \frac{1}{E_{MW}} \right)$$

where $E_{MW}$ represents the molecular weight of ethanol (g/mol).

Similarly, mean fluxes for glycerol (Q4), and acetic acid (Q7) can be calculated. The stoichiometric matrix St discussed above can thus be rearranged to separate measured and unmeasured fluxes as follows:

$$St \times Q = St_{unmeasured} \times Q_{unmeasured} + St_{measured} \times Q_{measured}$$

$$St \times Q = \begin{bmatrix} 0 & 1 & -1 & -1 \\ 0 & 0 & 0.67 & 0 \\ 0.23 & 1/3 & 0 & 5/3 \\ -1.21 & -1 & 0 & 0 \end{bmatrix} \begin{pmatrix} Q2 \\ Q3 \\ Q4 \\ Q5 \end{pmatrix} + \begin{bmatrix} 0 & 0 & 0 & 0 \\ 0 & -1 & 0 & -1 \\ 0 & -0.5 & -1/3 & 0.5 \\ 1 & 0 & -1 & 0 \end{bmatrix} \begin{pmatrix} Q1 \\ Q8 \\ Q4 \\ Q7 \end{pmatrix}$$

The unmeasured fluxes can be determined by rearranging this preceding equation as follows:

$$Q_{unmeasured} = -ST_{unmeasured}^{-1} \times ST_{measured} \times Q_{measured}$$

After thus obtaining $Q_{unmeasured}$ from $Q_{measured}$, yeast cell mass and $CO_2$ can be estimated as follows:

$$\begin{pmatrix} Cellmass \\ CO_2 \end{pmatrix} = \begin{bmatrix} 23.82 \\ 44 \end{bmatrix} \begin{bmatrix} 1 & 0 & 0 & 0 \\ 0.21 & 0 & 1/3 & 1 \end{bmatrix} \begin{pmatrix} Q2 \\ Q3 \\ Q5 \\ Q6 \end{pmatrix}$$

Figure 4:
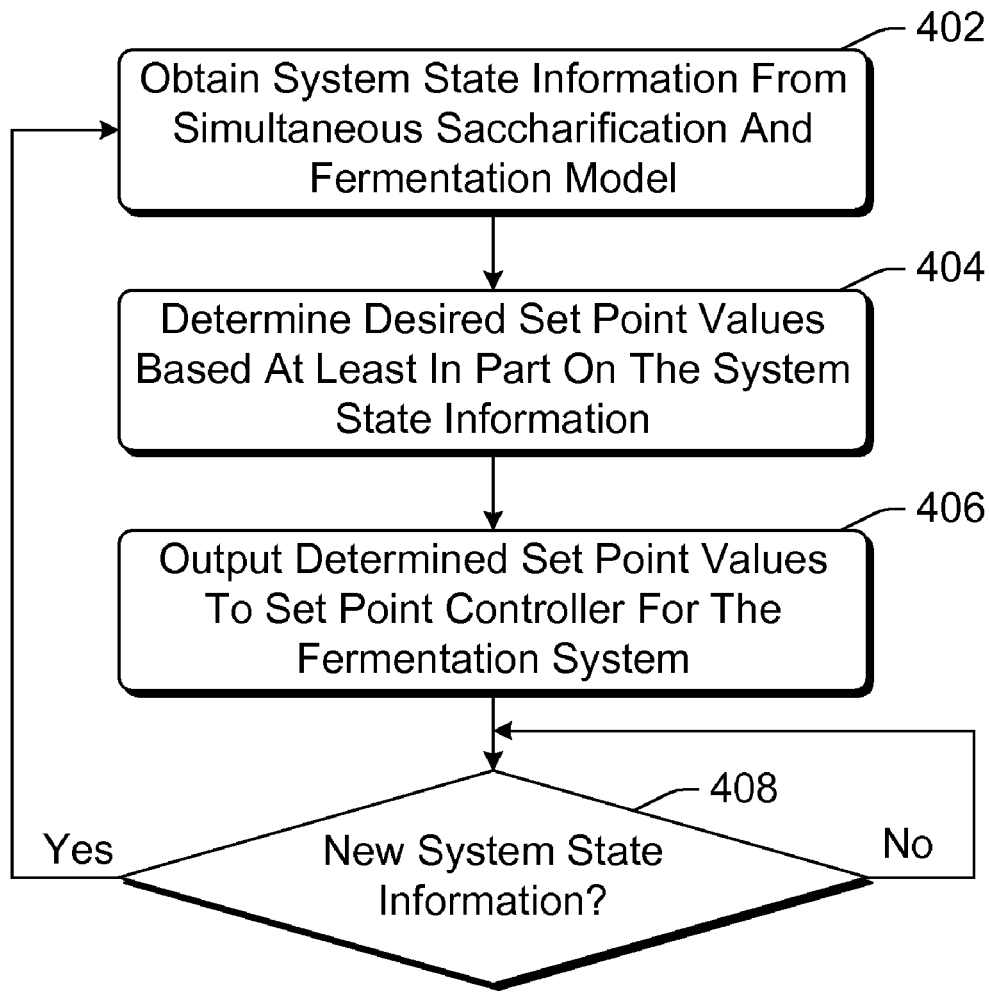
FIG. 4 is a flowchart illustrating an example process for generating and using the set point values for a fermentation system in accordance with one or more embodiments.

Returning to FIG. 1, dynamic fermentation controller 104 dynamically updates the set point values in order to increase the final ethanol concentration in fermenter system 102, and thus the ethanol output of the fermenter system 102. FIG. 4 is a flowchart illustrating an example process 400 for generating and using the set point values for a fermentation system in accordance with one or more embodiments. Process 400 is performed, for example, by dynamic fermentation controller 104 of FIG. 1, or control module 216 of FIG. 2. Process 400 can be performed in software, firmware, hardware, and/or combinations thereof.

Initially, system state information is obtained from the simultaneous saccharification and fermentation model (act 402). The SSF model changes as the fermentation system generates ethanol, these changes reflecting changes in the fermentation system. When the fermentation system begins operation, one or more of the parameters may be initially estimated based on prior experience. These initial estimates are the initial values used as the system state information, and can (and typically will) be changed as the fermentation system operates.

The system state information is then used as the basis for determining desired set point values (act 404). The desired set point values are values that can be used by a set point controller to modify the parameters and/or inputs of the fermentation system. These parameters and/or inputs include, for example, values for temperature of the fermentation system, pH of the fermentation system, and enzyme dosage input to the fermentation system. These parameters and/or inputs are determined so as to increase the final ethanol concentration in the fermentation system.

The set point values determined in act 404 are then output to one or more set point controllers for the fermentation system (act 406). The set point controller(s) uses these set point values to adjust the parameters and/or inputs to the fermentation system. For example, as discussed above with respect to FIG. 2, these set point values can be used to adjust the amount of enzyme input to the fermentation system, the temperature of the fermentation system, and the pH of the fermentation system.

Process 400 then waits until new system state information has been determined (act 408). Once new system state information is detected as being available, process 400 returns to act 402 to determine new set point values based on the new system state information. Thus, as can be seen in process 400, the parameters and/or inputs of the fermentation system can be changed during the fermentation process based on the system state information from the simultaneous saccharification and fermentation model.

The model for SSF based on the yeast model and saccharification model as discussed above is the basis for the dynamic fermentation controller determining the set point values. The SSF model discussed above can be reformulated into matrix notation with system states $x_1 \ldots x_{11}$ and control variables $u_1$, $u_2$, and $u_3$ as follows:

$$\begin{bmatrix} x_1 \\ x_2 \\ x_3 \\ x_4 \\ x_5 \\ x_6 \\ x_7 \\ x_8 \\ x_9 \\ x_{10} \\ x_{11} \end{bmatrix} = \begin{bmatrix} X \\ G \\ E \\ O \\ EM \\ SM \\ e_1 \\ e_2 \\ e_3 \\ e_4 \\ GP \end{bmatrix} \quad \begin{bmatrix} u_1 \\ u_2 \\ u_3 \end{bmatrix} = \begin{bmatrix} T \\ pH \\ GA \end{bmatrix}$$

The following system equations then apply:

$$f_1(x, u, t) = (r_3 - D)x_1 + \eta_3(0.1212u_1) + \eta_4\left(-H_{u_1,37}\left(\frac{u_1 - 33}{37 - 33}\right)\right)$$

$$f_2(x, u, t) = -\left(\frac{r_1 v_1}{Y_1} + \frac{r_2 v_2}{Y_2} + \frac{r_4 y_4}{Y_3}\right)x_1 + (G_0 - x_2)D + \eta_0 H_{x_{11},0} GA_{activity}(u_1, u_2)u_3$$

$$f_3(x, u, t) = \left(\phi_1 \frac{r_1 v_1}{Y_1}\right)x_1 - x_3 D$$

$$f_4(x, u, t) = -\left(\phi_2 \frac{r_4 v_4}{Y_3}\right)x_1 + (K_{La}O^* - Dx_4)$$

$$f_5(x, u, t) = \left(r_1 v_1 + r_4 v_4 - \frac{r_3 v_1}{\alpha_2}\right)x_1 - \eta_1\left(\frac{1229.56 C_{aa}}{10^{u_2 - 4.71} + 1}\right)$$

$$f_6(x, u, t) = \left(r_2 v_2 - \frac{r_3 v_1}{\alpha_2}\right)x_1 - \eta_2 H_{u_2,5.0}(0.725 u_2)$$

$$f_7(x, u, t) = \alpha \psi_1 \left(\frac{x_2}{K_1 + x_2}\right) - x_7 \beta + \alpha^*$$

$$f_8(x, u, t) = \alpha \psi_2 \left(\frac{x_2}{K_1 + x - 2}\right) - x_8 \beta + \alpha^*$$

$$f_9(x, u, t) = \alpha \psi_3 \left(\frac{x_5}{K_2 + x_5}\right)\left(\frac{x_6}{K_3 + x_6}\right) - x_9 \beta + \alpha^*$$

$$f_{10}(x, u, t) = \alpha \psi_4 \left(\frac{x_2}{K_1 + x_2}\right)\left(\frac{x_4}{K_4 + x_4}\right) - x_{10} \beta + \alpha^*$$

$$f_{11}(x, u, t) = -\eta_0 GA_{activity}(u_1, u_2)u_3$$

These system equations can be compactly represented as:

$$\dot{x}_i = f_i(x, u, t) \text{ where } i = 1 \text{ to } 11$$

The dynamic fermentation controller attempts to increase the value of $x_3$, which is the final ethanol concentration. At the same time, the controller attempts to reduce the deviation of $x_2$ from a set point (e.g., a value of 20) during operation. The value of 20 represents the glucose concentration of 20 g/L, which has been assumed to be the minimum level that does not adversely affect the SSF process. Alternatively, this, value for $x_2$ could be higher or lower than 20.

The dynamic fermentation controller further operates subject to the following constraints:

$\dot{x}_i = f_i(x,u,t)$ (the system dynamics discussed above)

$x(t_0) = x_0$ (initial condition equality constraints)

$u_{1,min}(20) \leq u_1 \leq u_{1,max}(35)$ (temperature limits)

$u_{2,min}(3.5) \leq u_2 \leq u_{2,max}(5.0)$ (pH limits)

$\frac{du_3}{dt} \geq 0$ (enzyme dosage limits)

Where $u_{i,min}$ refers to the minimum constraint on control variable $u_i$, and $u_{i,max}$ refers to the maximum constraint on control variable $u_i$.

These temperature, pH, and enzyme dosage limits constraints can be rewritten as equality constraints in matrix form as follows:

$$U = \begin{bmatrix} \Gamma_1^2(u_{1,max}-u_1)(u_1-u_{1,min})-1 \\ \Gamma_2^2(u_{2,max}-u_2)(u_2-u_{2,min})-1 \\ \Gamma_3^2(u_{3,max}-u_3)(u_3-u_{3,min})-1 \end{bmatrix}$$

Where $\Gamma_1$, $\Gamma_2$, and $\Gamma_3$ are constants (e.g., $\Gamma_1=100$, $\Gamma_2=500$ and $\Gamma_3=1$). The control vector constraints can then be written as:

$(u_{1,max}-u_1)(u_1-u_{1,min}) = \Gamma_1^{-2}$ $(u_{2,max}-u_2)(u_2-u_{2,min}) = \Gamma_2^{-2}$ $(u_{3,max}-u_3)(u_3-u_{3,min}) = \Gamma_3^{-2}$ A cost function J for the dynamic fermentation controller operation can then be written as follows:

$$J = \theta(x,t)\Big|_{t_0}^{t_f} + \int_{t_0}^{t_f} \{\phi(x,u,t) + \lambda[f_i(x,u,t)-\dot{x}] + (UH_{U,0})^T\} dt$$

By solving function J, a control vector that reduces the cost function for the current system state information can be obtained.

In the cost function J, the $\theta(x,t)|_{t_0}^{t_f}$ term defines the process goal (increasing final ethanol concentration) that is to be achieved at the final time, subject to the initial state constraints. The $\phi(x,u,t)$ term defines the second goal (reducing the deviation from the glucose set point) during the SSF process. The $\lambda[f_i(x,u,t)-\dot{x}]$ term accounts for the system dynamic constraint, where the parameter $\lambda$ is the Lagrange multiplier that converts vector constraints into a scalar quantity called Hamiltonian $\mathcal{H}$ (discussed in more detail below) and transforms a vector performance index (defined by $\phi(x,u,t)$) to a scalar minimization problem (defined in terms of J maximization/minimization). The $(UH_{U,0})^T$ term determines the penalty function for deviations outside the allowed ranges for the control variables. The magnitude of the penalty function depends on constants $\Gamma_1$, $\Gamma_2$, and $\Gamma_3$ discussed above.

The Hamiltonian $\mathcal{H}$ is defined as:

$$\mathcal{H} = \phi(x,u,t) + \lambda^T f(x,u,t) + (UH_{U,0})^T$$

Using the Hamiltonian $\mathcal{H}$ the cost function J can be rewritten as:

$$J = (\theta(x,t) - \lambda^T x)\Big|_{t_0}^{t_f} + \int_{t_0}^{t_f} + \int_{t_0}^{t_f} (\mathcal{H} - \lambda^T \dot{x} + (U^T H_{U,0})) dt$$

Based on a variational calculus approach, the variation in J can be calculated as:

$$\delta J = \delta x^T \left[\frac{\partial \theta}{\partial x} - \lambda\right]\Big|_{t_0}^{t_f} + \int_{t_0}^{t_f} \left(\delta x^T \left[\frac{\partial \mathcal{H}}{\partial x} + \dot{\lambda}\right] + \delta u^T \left[\frac{\partial \mathcal{H}}{\partial u} + \frac{\partial ((UH_{U,0})^T)}{\partial u}\right]\right) dt$$

At its optimum, $\delta J = 0$, so that $$\frac{\partial \theta}{\partial x} - \lambda = 0$$

at $t = t_f$ and $\delta x^T = 0$ at $t = t_0$ (for given initial conditions $x_0$), and:

$$\frac{\partial \mathcal{H}}{\partial x} = -\dot{\lambda} = \frac{\partial \phi}{\partial x} + \frac{\partial f^T}{\partial x} \lambda \text{ at any } t$$

$$\frac{\partial \mathcal{H}}{\partial u} = \frac{\partial \phi}{\partial u} + \frac{\partial f^T}{\partial u} \lambda$$

However, for any choice of non-optimum u:

$$\frac{\partial \mathcal{H}}{\partial u} + \frac{\partial ((UH_{U,0})^T)}{\partial u} \neq 0$$

Therefore, u is modified such that J is minimized by choosing $\Delta J \leq 0$, where:

$$\Delta J = \int_{t_0}^{t_f} \left(\left[\frac{\partial \mathcal{H}}{\partial u} + \frac{\partial ((UH_{U,0})^T)}{\partial u}\right]\right) \Delta u dt$$

In order to minimize J, $\Delta u$ should be chosen such that $\Delta J \leq 0$. A choice of $\Delta u$ that satisfies this criterion is:

$$\Delta u = -k(t)\left[\frac{\partial \mathcal{H}}{\partial u} - \frac{\partial ((UH_{U,0})^T)}{\partial u}\right]$$

Where k(t) is a parameter gain matrix.

Absolute change in u is determined by the parameter gain matrix k(t). Absolute values of different control variables, such as temperature, pH, and glucoamylase amount are dependent on the sensitivity of the SSF process to changes in these variables. So, the values in k(t) are chosen (e.g., based on prior trial and error using model predictions) to account for the differences in the sensitivity of the control variables. The values of k(t) can vary, and example values of $k_1(t)$, $k_2(t)$, and $k_3(t)$, corresponding to the values $u_1$, $u_2$, and $u_3$, respectively, are: $k_1(t)=0.005$, $k_2(t)=0.001$ and $k_3(t)=0.0001$. In general, k(t) is dependent on total fermentation time and is a function of time.

Accordingly, ΔJ can be rewritten as:

$$\Delta J = -\int_{t_0}^{t_f} \left( k(t) \left[ \left(\frac{\partial \mathcal{H}}{\partial u}\right)^2 - \left(\frac{\partial ((UH_{U,0})^T)}{\partial u}\right)^2 \right] \right) dt$$

Values of u are then calculated so that the change in the cost function J is less than a small number ε (e.g., ε<0.01).

Various different processes can be used to calculate such values of u. In one or more embodiments, a steepest descent algorithm is used to iteratively calculate the changes in u until the change in the cost function J is less than a small number ε. The steepest descent algorithm calculates a control vector for a given system x=f(x,u,t) with initial conditions $x(0)=x_0$ and constraints $u_{i,min} \leq u_i \leq u_{i,max}$ on the control vector.

Figure 5:
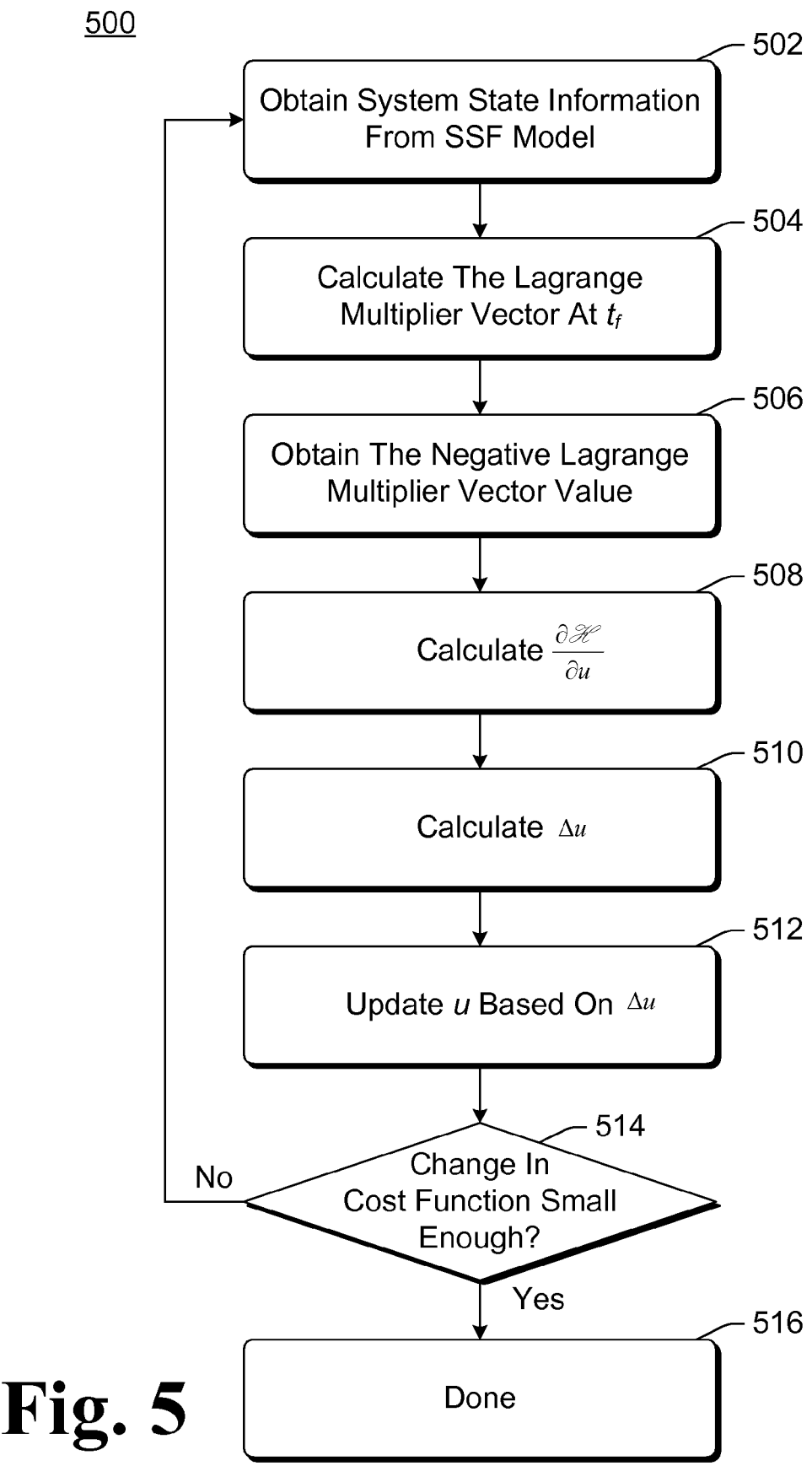
FIG. 5 is a flowchart illustrating an example process for determining the set point values in accordance with one or more embodiments.

FIG. 5 is a flowchart illustrating an example process 500 for determining the set point values in accordance with one or more embodiments. Process 500 is performed, for example, by dynamic fermentation controller 104 of FIG. 1, or control module 216 of FIG. 2. Process 400 can be performed in software, firmware, hardware, and/or combinations thereof. The set point values are calculated as the values $u_1$, $u_2$, and $u_3$, also referred to as the control vector u.

Initially, the system state information from the SSF model is obtained (act 502). The Lagrange multiplier vector at $t_f$ is then calculated (act 504) as follows:

$$\lambda(t_f) = \left(\frac{\partial \theta}{\partial x}\right)_{t=t_f}$$

The negative Lagrange multiplier vector value is then calculated (act 506) by solving the following backwards in time with given initial conditions $\lambda(t_f)$:

$$-\dot{\lambda} = \frac{\partial \phi}{\partial x} + \frac{\partial f^T}{\partial x} \lambda$$

Given these values, a value of $$\frac{\partial \mathcal{H}}{\partial u}$$

is calculated (act 508) as follows:

$$\frac{\partial \mathcal{H}}{\partial u} = \frac{\partial \phi}{\partial u} + \frac{\partial f^T}{\partial u} \lambda$$

Given $$\frac{\partial \mathcal{H}}{\partial u},$$

a value of Δu is set as follows:

$$\Delta u = -k(t) \left[ \frac{\partial \mathcal{H}}{\partial u} - \frac{\partial ((UH_{U,0})^T)}{\partial u} \right]$$

The value of u is then updated based on Δu (act 512) as follows:

$$u(t)^{n+1} = u(t)^n + \Delta u(t)$$

Given the updated value of u, a check is then made as to whether the change in the cost function is small enough (act 514). This check is performed as follows:

$$|u(t)^{n+1} - u(t)^n < \epsilon|$$

If the change is small enough, then the process is done and the most recently updated values of u in act 512 are the set point values $u_1$, $u_2$, and $u_3$. However, if the change is not small enough, then process 500 returns to act 502 to obtain new system state information from the SSF model based on the most recently updated values of u in act 512.

In the above discussions of the operation of the dynamic fermentation controller, various terms are discussed. The following are example values for these terms that are used in one or more embodiments of the dynamic fermentation controller, although other values can alternatively be used.

$$\theta(x, t) = -x_3$$

$$\phi(x, u, t) = (x_2 - 20)^2$$

$$\frac{\partial \theta}{\partial x}\bigg|_{t=t_f} = [0 \ 0 \ -1 \ 0 \ 0 \ 0 \ 0 \ 0 \ 0]$$

$$\frac{\partial \theta}{\partial u} = [0 \ 0 \ 0]$$

$$\frac{\partial \phi}{\partial x} = [0 \ 2(x_2 - 20) \ 0 \ 0 \ 0 \ 0 \ 0 \ 0 \ 0]$$

$$\frac{\partial \phi}{\partial u} = [0 \ 0 \ 0]$$

$$\frac{\partial U^T}{\partial x} = 0$$

$$\frac{\partial U^T}{\partial u} = \begin{bmatrix} 2u_1 - (u_{1,max} + u_{1,min}) \\ 2u_2 - (u_{2,max} + u_{2,min}) \\ 2u_3 - (u_{3,max} + u_{3,min}) \end{bmatrix}^T$$

$$\frac{\partial f^T}{\partial x} = \begin{bmatrix} \frac{\partial f_1}{\partial x_1} & \cdots & \frac{\partial f_1}{\partial x_{11}} \\ \vdots & \frac{\partial f_2}{\partial x_2} & \vdots \\ & & \ddots \\ & & & \frac{\partial f_{11}}{\partial x_{11}} \end{bmatrix}$$

$$\frac{\partial f^T}{\partial u} = \begin{bmatrix} \frac{\partial f_1}{\partial u_1} & \frac{\partial f_1}{\partial u_2} & \frac{\partial f_1}{\partial u_3} \\ \vdots & \frac{\partial f_2}{\partial u_2} & \vdots \\ & \vdots & \\ & & \frac{\partial f_{11}}{\partial u_3} \end{bmatrix}$$

Examples of the terms in the matrices $$\frac{\partial f^T}{\partial x} \text{ and } \frac{\partial f^T}{\partial u}$$

can be calculated as follows:

$$\frac{\partial f_1}{\partial x_1} = (r_3 - D)$$

$$\frac{\partial f_1}{\partial x_2} = \frac{\partial f_1}{\partial x_4} = \frac{\partial f_1}{\partial x_7} = \frac{\partial f_1}{\partial x_8} = \frac{\partial f_1}{\partial x_{10}} = \frac{\partial f_1}{\partial x_{11}} = 0$$

$$\frac{\partial f_1}{\partial x_3} = \eta_4(-H_{x_3,95})u_1$$

$$\frac{\partial f_1}{\partial x_5} = \mu_3 x_9 x_1 \left[\frac{1}{k_3+k_5} - \frac{x_5}{(k_3+x_5)^2}\right]\left(\frac{x_6}{k_4+x_6}\right)$$

$$\frac{\partial f_1}{\partial x_6} = \frac{r_3 x_3 k_4}{x_6(k_4+x_6)}$$

$$\frac{\partial f_1}{\partial x_9} = \frac{r_3 r_1}{x_9}$$

$$\frac{\partial f_2}{\partial x_1} = -\left(\frac{r_1 v_1}{Y_1} + \frac{r_2 v_2}{Y_2} + \frac{r_4 v_4}{Y_3}\right)$$

$$\frac{\partial f_2}{\partial x_2} = -\frac{v_1 r_1}{Y_1} x_1 \left(\frac{k_1}{x_2} - \left(\frac{\frac{H_{x_2,150}}{330-150}}{1 - H_{x_2,150}\left(\frac{x_2-95}{330-150}\right)}\right)\right) -$$

$$\frac{v_2 r_2}{Y_2} x_1 \left(\frac{k_2}{x_2} - \left(\frac{\frac{H_{x_2,150}}{330-150}}{1 - H_{x_2,150}\left(\frac{x_2-95}{330-150}\right)}\right)\right) - \frac{v_4 r_4 k_2}{Y_3 x_2} - D$$

$$\frac{\partial f_2}{\partial x_3} = \left(\frac{v_1 x_1 r_1}{Y_1} + \frac{v_2 x_1 r_2}{Y_2}\right)\left(\frac{\frac{H_{x_3,95}}{150-95}}{1 - H_{x_3,95}\left(\frac{x_3-95}{150-95}\right)}\right)$$

$$\frac{\partial f_2}{\partial x_4} = -\left(\frac{x_1 r_4 v_4}{Y_3}\right)\frac{k_5}{x_4(k_5+x_4)}$$

$$\frac{\partial f_2}{\partial x_5} = \frac{\partial f_2}{\partial x_6} = \frac{\partial f_2}{\partial x_9} = \frac{\partial f_2}{\partial x_{11}} = 0$$

$$\frac{\partial f_2}{\partial x_7} = -\left(\frac{r_1 v_1}{Y_1 x_7}\right) x_1$$

$$\frac{\partial f_2}{\partial x_8} = -\left(\frac{r_2 v_2}{Y_2 x_8}\right) x_1$$

$$\frac{\partial f_2}{\partial x_{10}} = -\left(\frac{r_4 v_4}{Y_3 x_{10}}\right) x_1$$

$$\frac{\partial f_3}{\partial x_1} = \phi_1 \frac{r_1 v_1}{Y_1}$$

$$\frac{\partial f_3}{\partial x_2} = \phi_1 \frac{r_1 v_1}{Y_1}\left(\frac{r_1 k_1}{x_2}\right)$$

$$\frac{\partial f_3}{\partial x_3} = \phi_1 \frac{r_1 v_1 x_1}{Y_1}\left[\frac{\frac{-H_{x_3,95}}{150-95}}{1 - H_{x_3,95}\left(\frac{x_3-95}{150-95}\right)}\right]$$

$$\frac{\partial f_3}{\partial x_4} = \frac{\partial f_3}{\partial x_5} = \frac{\partial f_3}{\partial x_6} = \frac{\partial f_3}{\partial x_8} = \frac{\partial f_3}{\partial x_9} = \frac{\partial f_3}{\partial x_{10}} = \frac{\partial f_3}{\partial x_{11}} = 0$$

-continued $$\frac{\partial f_3}{\partial x_7} = \phi_1 \frac{r_1 v_1 x_1}{Y_1 x_7}$$

$$\frac{\partial f_4}{\partial x_1} = -\left(\frac{\phi_2 r_4 v_4}{Y_3}\right)$$

$$\frac{\partial f_4}{\partial x_2} = -\left(\frac{\phi_2 r_4 v_4 k_1 x_1}{Y_3 x_2}\right)$$

$$\frac{\partial f_4}{\partial x_3} = \frac{\partial f_4}{\partial x_5} = \frac{\partial f_4}{\partial x_6} = \frac{\partial f_4}{\partial x_7} = \frac{\partial f_4}{\partial x_8} = \frac{\partial f_4}{\partial x_9} = \frac{\partial f_4}{\partial x_{11}} = 0$$

$$\frac{\partial f_4}{\partial x_4} = -\left(\frac{\phi_2 r_4 v_4 k_5 x_1}{Y_3 x_4}\right) - D$$

$$\frac{\partial f_4}{\partial x_{10}} = -\left(\frac{\phi_2 r_4 v_4 x_1}{Y_3 x_{10}}\right)$$

$$\frac{\partial f_5}{\partial x_1} = \left(r_1 v_1 + r_4 v_4 - \frac{r_3 \mu_3}{\alpha_1}\right)$$

$$\frac{\partial f_5}{\partial x_2} = r_1 v_1 x_1 \left[\frac{\frac{-H_{x_2,150}}{330-150}}{1 - H_{x_2,150}\left(\frac{x_2-150}{330-150}\right)}\right] + \frac{r_4 v_4 k_2 x_1}{x_2}$$

$$\frac{\partial f_5}{\partial x_3} = r_1 v_1 x_1 \left[\frac{\frac{-H_{x_3,95}}{150-95}}{1 - H_{x_3,95}\left(\frac{x_3-95}{150-95}\right)}\right]$$

$$\frac{\partial f_5}{\partial x_4} = \frac{r_4 v_4 k_5 x_1}{x_4}$$

$$\frac{\partial f_5}{\partial x_5} = -\frac{r_3 v_3 k_3 x_1}{\alpha_1 x_5}$$

$$\frac{\partial f_5}{\partial x_6} = -\frac{r_3 v_3 k_4 x_1}{\alpha_1 x_6}$$

$$\frac{\partial f_5}{\partial x_7} = \frac{r_1 v_1 x_1}{x_7}$$

$$\frac{\partial f_5}{\partial x_8} = \frac{\partial f_5}{\partial x_{11}} = 0$$

$$\frac{\partial f_5}{\partial x_9} = -\frac{r_3 v_3 x_1}{\alpha_1 x_9}$$

$$\frac{\partial f_5}{\partial x_{10}} = \frac{r_4 v_4 x_1}{x_{10}}$$

$$\frac{\partial f_6}{\partial x_1} = \left(r_2 v_2 - \frac{r_3 v_3}{\alpha_2}\right)$$

$$\frac{\partial f_6}{\partial x_2} = r_2 v_2 x_2 \left[\frac{k_2}{x_2} - \left(\frac{\frac{-H_{x_2,150}}{330-150}}{1 - H_{x_2,150}\left(\frac{x_2-150}{330-150}\right)}\right)\right]$$

$$\frac{\partial f_6}{\partial x_3} = r_2 v_2 x_1 \left[-\left(\frac{\frac{-H_{x_2,150}}{330-150}}{1 - H_{x_2,150}\left(\frac{x_2-150}{330-150}\right)}\right)\right]$$

$$\frac{\partial f_6}{\partial x_4} = \frac{\partial f_6}{\partial x_7} = \frac{\partial f_6}{\partial x_{10}} = \frac{\partial f_6}{\partial x_{11}} = 0$$

$$\frac{\partial f_6}{\partial x_5} = -\frac{r_3 v_3 k_3 x_1}{\alpha_2 x_5}$$

$$\frac{\partial f_6}{\partial x_6} = -\frac{r_3 v_3 x_1 k_4}{\alpha_2 x_6}$$

$$\frac{\partial f_6}{\partial x_8} = -\frac{r_2 v_2 x_1}{x_8}$$

$$\frac{\partial f_6}{\partial x_9} = -\frac{r_3 v_3 x_1}{\alpha_2 x_9}$$

-continued $$\frac{\partial f_7}{\partial x_1} = \frac{\partial f_7}{\partial x_3} = \frac{\partial f_7}{\partial x_4} = \frac{\partial f_7}{\partial x_5} = \frac{\partial f_7}{\partial x_6} = \frac{\partial f_7}{\partial x_8} = \frac{\partial f_7}{\partial x_9} = \frac{\partial f_7}{\partial x_{10}} = \frac{\partial f_7}{\partial x_{11}} = 0$$

$$\frac{\partial f_7}{\partial x_2} = \frac{\psi_1 k_1}{(k_1 + x_2)^2}$$

$$\frac{\partial f_7}{\partial x_7} = -\beta$$

$$\frac{\partial f_8}{\partial x_1} =$$

$$\frac{\partial f_8}{\partial x_3} = \frac{\partial f_8}{\partial x_4} = \frac{\partial f_8}{\partial x_5} = \frac{\partial f_8}{\partial x_6} = \frac{\partial f_8}{\partial x_7} = \frac{\partial f_8}{\partial x_8} = \frac{\partial f_8}{\partial x_9} = \frac{\partial f_8}{\partial x_{10}} = \frac{\partial f_8}{\partial x_{11}} = 0$$

$$\frac{\partial f_8}{\partial x_2} = \frac{\psi_2 k_2}{(k_2 + x_2)^2}$$

$$\frac{\partial f_9}{\partial x_1} = \frac{\partial f_9}{\partial x_2} = \frac{\partial f_9}{\partial x_3} = \frac{\partial f_9}{\partial x_4} = \frac{\partial f_9}{\partial x_7} = \frac{\partial f_9}{\partial x_8} = \frac{\partial f_9}{\partial x_{10}} = \frac{\partial f_9}{\partial x_{11}} = 0$$

$$\frac{\partial f_9}{\partial x_5} = \psi_3 \frac{x_5}{(k_3 + x_5)^2} \left(\frac{x_6}{k_4 + x_6}\right)$$

$$\frac{\partial f_9}{\partial x_6} = \psi_3 \frac{x_5}{k_3 + x_5} \left(\frac{k_4}{(k_4 + x_6)^2}\right)$$

$$\frac{\partial f_9}{\partial x_9} = -\beta$$

$$\frac{\partial f_{10}}{\partial x_1} = \frac{\partial f_{10}}{\partial x_3} = \frac{\partial f_{10}}{\partial x_5} = \frac{\partial f_{10}}{\partial x_6} = \frac{\partial f_{10}}{\partial x_7} = \frac{\partial f_{10}}{\partial x_8} = \frac{\partial f_{10}}{\partial x_9} = \frac{\partial f_{10}}{\partial x_{11}} = 0$$

$$\frac{\partial f_{10}}{\partial x_2} = \psi_3 \frac{x_4}{k_5 + x_4} \left(\frac{k_1}{(k_1 + x_2)^2}\right)$$

$$\frac{\partial f_{10}}{\partial x_4} = \psi_3 \frac{k_5}{(k_5 + x_4)^2} \left(\frac{x_2}{k_1 + x_2}\right)$$

$$\frac{\partial f_{10}}{\partial x_{10}} = -\beta$$

$$\frac{\partial f_{11}}{\partial x_1} = \frac{\partial f_{11}}{\partial x_2} = \frac{\partial f_{11}}{\partial x_3} =$$

$$\frac{\partial f_{11}}{\partial x_4} = \frac{\partial f_{11}}{\partial x_5} = \frac{\partial f_{11}}{\partial x_6} = \frac{\partial f_{11}}{\partial x_7} = \frac{\partial f_{11}}{\partial x_8} = \frac{\partial f_{11}}{\partial x_9} = \frac{\partial f_{11}}{\partial x_{10}} = \frac{\partial f_{11}}{\partial x_{11}} = 0$$

$$\frac{\partial f_1}{\partial u_1} = \eta_1[-H_{x_3,95}(x_3 - 95)] + \eta_5\left[-H_{u_1,15}e^{\left(\frac{u_1 - u_{1,min}}{u_{1,max} - u_{1,min}}\right)}\right]$$

$$\frac{\partial f_1}{\partial u_2} = \frac{\partial f_1}{\partial u_3} = 0$$

$$\frac{\partial f_2}{\partial u_1} = 0$$

$$\frac{\partial f_2}{\partial u_2} = -\frac{\partial}{\partial u_2} GA_{activity}(u_1, u_2) u_3$$

$$\frac{\partial f_2}{\partial u_3} = -GA_{activity}(u_1, u_2)$$

$$\frac{\partial f_3}{\partial u_1} = \frac{\partial f_3}{\partial u_2} = \frac{\partial f_3}{\partial u_3} = 0$$

$$\frac{\partial f_4}{\partial u_1} = \frac{\partial f_4}{\partial u_2} = \frac{\partial f_4}{\partial u_3} = 0$$

$$\frac{\partial f_5}{\partial u_1} = \frac{\partial f_5}{\partial u_3} = 0$$

$$\frac{\partial f_5}{\partial u_2} = \eta_1\left(\frac{1229.56 C_{aa}}{(10^{u_2 - 4.71} + 1)^2}\right)(\log 10) 10^{(u_2 - 4.74)}$$

$$\frac{\partial f_6}{\partial u_1} = \frac{\partial f_6}{\partial u_3} = 0$$

$$\frac{\partial f_6}{\partial u_2} = \eta_2 H_{u_2,5.0}(0.725)$$

$$\frac{\partial f_7}{\partial u_1} = \frac{\partial f_7}{\partial u_2} = \frac{\partial f_7}{\partial u_3} = 0$$

-continued $$\frac{\partial f_8}{\partial u_1} = \frac{\partial f_8}{\partial u_2} = \frac{\partial f_8}{\partial u_3} = 0$$

$$\frac{\partial f_9}{\partial u_1} = \frac{\partial f_9}{\partial u_2} = \frac{\partial f_9}{\partial u_3} = 0$$

$$\frac{\partial f_{10}}{\partial u_1} = \frac{\partial f_{10}}{\partial u_2} = \frac{\partial f_{10}}{\partial u_3} = 0$$

$$\frac{\partial f_{11}}{\partial u_1} = \frac{\partial f_{11}}{\partial u_2} = \frac{\partial f_{11}}{\partial u_3} = 0$$

Figure 6:
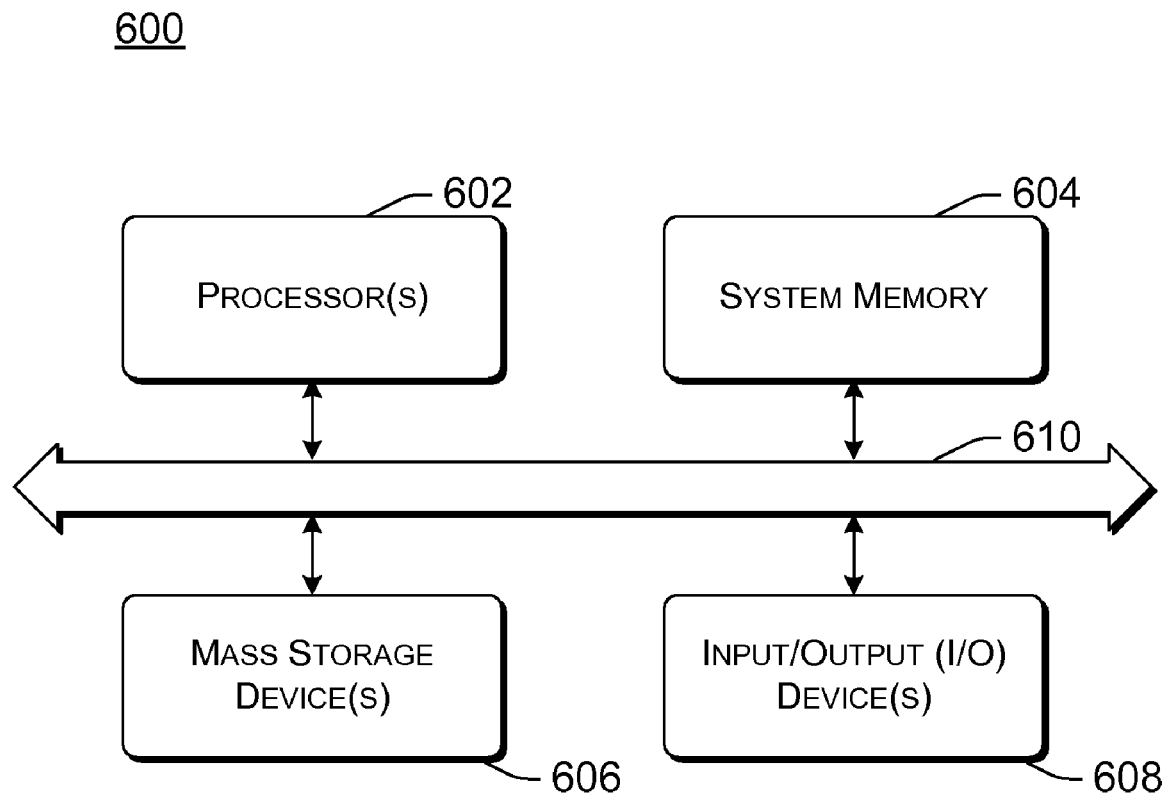
FIG. 6 is a block diagram illustrating an example computing device in accordance with one or more embodiments.

FIG. 6 is a block diagram illustrating an example computing device 600. Computing device 600 can be used to implement the various techniques and processes discussed herein. For example, computing device 600 may implement dynamic fermentation controller 104 of FIG. 1 or control module 216 of FIG. 2. By way of another example, any of the processes discussed herein can be implemented by a processor(s) of computing device 600 executing instructions stored on one or more computer readable media. Computing device 600 can be any of a wide variety of computing devices, such as a desktop computer, a server computer, a handheld computer, a dedicated controller, and so forth.

Computing device 600 includes one or more processor(s) 602, system memory 604, mass storage device(s) 606, input/output (I/O) device(s) 608, and bus 610. Processor(s) 602 include one or more processors or controllers that execute instructions stored in system memory 604 and/or mass storage device(s) 606. Processor(s) 602 may also include computer readable media, such as cache memory.

System memory 604 includes various computer readable media, including volatile memory (such as random access memory (RAM)) and/or nonvolatile memory (such as read only memory (ROM)). System memory 604 may include rewritable ROM, such as Flash memory. System memory 604 includes removable and/or nonremovable media.

Mass storage device(s) 606 include various computer readable media, such as magnetic disks, optical disks, solid state memory (e.g., flash memory), and so forth. Various drives may also be included in mass storage device(s) 606 to enable reading from and/or writing to the various computer readable media. Mass storage device(s) 606 include removable media and/or nonremovable media.

I/O device(s) 608 include various devices that allow data and/or other information to be input to and/or output from computing device 600. Examples of I/O device(s) 608 include cursor control devices, keypads, microphones, monitors or other displays, speakers, printers, network interface cards, modems, lenses, CCDs or other image capture devices, and so forth.

Bus 610 allows processor(s) 602, system memory 604, mass storage device(s) 606, and I/O device(s) 608 to communicate with one another. Bus 610 can be one or more of multiple types of buses, such as a system bus, PCI bus, IEEE 1394 bus, USB bus, and so forth.

It should be noted that computing device 600 is only an example, and that various additional components may be included in device 600 and/or various components illustrated in FIG. 6 may not be included in device 600. For example, additional buses and/or devices may be included in device 600. By way of another example, mass storage device 606 may not be included in device 600. By way of another example, device 600 may be implemented as a single controller incorporating both a processor (e.g., processor 602) and system memory (e.g., memory 604).

Alternatively, the techniques and processes discussed herein can be implemented in hardware rather than as instructions stored on one or more computer readable media that are executed by a processor(s). For example, one or more application specific integrated circuits (ASICs) or one or more programmable logic devices (PLDs) could be designed to implement the techniques and processes discussed herein.

Although the description above uses language that is specific to structural features and/or methodological acts, it is to be understood that the subject matter defined in the appended claims is not limited to the specific features or acts described. Rather, the specific features and acts are disclosed as example forms of implementing the claims.

What is claimed is:

1. A method for the production of ethanol comprising:
   receiving a temperature of a simultaneous saccharification and fermentation system;
   receiving a pH of the simultaneous saccharification and fermentation system;
   receiving information identifying amounts of components of a fermented mash generated by the simultaneous saccharification and fermentation system;
   generating, based at least in part on the temperature, the pH, and the information identifying amounts of components of the fermented mash, values for temperature, pH, and enzyme dosage for the simultaneous saccharification and fermentation system; and
   outputting the values to one or more controllers of the simultaneous saccharification and fermentation system wherein the generating and outputting values are based at least in part on a saccharification model that predicts concentrations of fermented mash or a fermentation model that predicts yeast metabolism, the one or more controllers allowing for the production of ethanol.

2. A method as recited in claim 1, further comprising repeating the generating and outputting each time a change in conditions in the simultaneous saccharification and fermentation system is detected.

3. A method as recited in claim 2, wherein the change in conditions comprises a change in temperature in the simultaneous saccharification and fermentation system.

4. A method as recited in claim 2, wherein the change in conditions comprises a change in pH in the simultaneous saccharification and fermentation system.

5. A method as recited in claim 2, wherein repeating the generating and outputting comprises:
   receiving system state information from a simultaneous saccharification and fermentation model that includes the saccharification model and the fermentation model, and that models the simultaneous saccharification and fermentation system; and
   repeating the generating and outputting each time the system state information changes.

6. A method as recited in claim 1, wherein the generating comprises generating the values for temperature, pH, and enzyme dosage based at least in part on a simultaneous saccharification and fermentation model of the simultaneous saccharification and fermentation system.

7. A method as recited in claim 6, wherein the simultaneous saccharification and fermentation model includes the saccharification model that predicts sugar concentration in a fermentation mash, and the fermentation model that simulates yeast metabolism.

8. A method as recited in claim 1, wherein generating the values for temperature, pH, and enzyme dosage comprises calculating new set point values repeatedly until a change in a cost function for the simultaneous saccharification and fermentation system is less than a threshold amount.

* * * * *